(12) United States Patent
Kassab

(10) Patent No.: US 10,779,750 B2
(45) Date of Patent: Sep. 22, 2020

(54) DEVICES, SYSTEMS, AND METHODS FOR REMOVING TARGETED LESIONS FROM VESSELS

(71) Applicant: 3DT Holdings, LLC, San Diego, CA (US)

(72) Inventor: Ghassan S. Kassab, La Jolla, CA (US)

(73) Assignee: 3DT Holdings, LLC, San Diego, CA (US)

( * ) Notice: Subject to any disclaimer, the term of this patent is extended or adjusted under 35 U.S.C. 154(b) by 109 days.

(21) Appl. No.: 15/470,958

(22) Filed: Mar. 28, 2017

(65) Prior Publication Data

US 2017/0196476 A1    Jul. 13, 2017

Related U.S. Application Data

(60) Continuation of application No. 12/748,166, filed on Mar. 26, 2010, now Pat. No. 9,603,545, which is a
(Continued)

(51) Int. Cl.
*A61B 5/053* (2006.01)
*A61B 5/107* (2006.01)
(Continued)

(52) U.S. Cl.
CPC .......... *A61B 5/0538* (2013.01); *A61B 5/0036* (2018.08); *A61B 5/01* (2013.01); *A61B 5/053* (2013.01); *A61B 5/1076* (2013.01); *A61B 5/417* (2013.01); *A61B 5/4836* (2013.01); *A61B 17/22* (2013.01); *A61B 17/22004* (2013.01); *A61B 17/320758* (2013.01); *A61B 18/02* (2013.01); *A61B 18/24* (2013.01); *A61B 18/245* (2013.01); *A61B 90/06* (2016.02); *A61F 2/958* (2013.01); *A61M 25/10184* (2013.11); *A61B 17/320725* (2013.01); *A61B 2017/00026* (2013.01); *A61B 2017/00084* (2013.01); *A61B 2017/22044* (2013.01); *A61B 2017/22061* (2013.01); *A61B 2018/0022* (2013.01); *A61B 2018/0212* (2013.01); *A61B 2090/061* (2016.02);
(Continued)

(58) Field of Classification Search
CPC ...... A61B 5/0538; A61B 18/245; A61B 5/053
See application file for complete search history.

(56) References Cited

U.S. PATENT DOCUMENTS

| 4,587,975 | A | * | 5/1986 | Salo | ................. A61B 5/0535 600/506 |
| 5,782,774 | A | * | 7/1998 | Shmulewitz | ......... A61B 5/0538 600/481 |

(Continued)

*Primary Examiner* — Richard G Louis
(74) *Attorney, Agent, or Firm* — Reichel Stohry Dean LLP; Mark C. Reichel; Natalie J. Dean

(57) ABSTRACT

Devices, systems, and methods for removing targeted lesions from vessels. In at least one embodiment of a device for removing a stenotic lesion from a vessel, the device comprises a sizing portion capable of measuring a luminal size parameter when at least part of the device is positioned within a lumen of a luminal organ, a typing portion, wherein at least part of the at least one typing portion is capable of physically touching a portion of the luminal organ or a structure therein, and a treatment portion capable of removing at least part of a stenotic lesion from the luminal organ.

19 Claims, 22 Drawing Sheets

Related U.S. Application Data continuation-in-part of application No. 12/428,656, filed on Apr. 3, 2009, now Pat. No. 8,465,452, which is a continuation-in-part of application No. 12/098,242, filed on Apr. 4, 2008, now Pat. No. 8,078,274, which is a continuation-in-part of application No. 11/891,981, filed on Aug. 14, 2007, now Pat. No. 8,114,143, which is a division of application No. 10/782,149, filed on Feb. 19, 2004, now Pat. No. 7,454,244.

(60) Provisional application No. 60/502,139, filed on Sep. 11, 2003, provisional application No. 60/493,145, filed on Aug. 7, 2003, provisional application No. 60/449,266, filed on Feb. 21, 2003.

(51) Int. Cl.

| | | |
|---|---|---|
| *A61B 5/00* | (2006.01) | |
| *A61B 17/22* | (2006.01) | |
| *A61B 17/3207* | (2006.01) | |
| *A61B 18/02* | (2006.01) | |
| *A61B 18/24* | (2006.01) | |
| *A61F 2/958* | (2013.01) | |
| *A61B 90/00* | (2016.01) | |
| *A61M 25/10* | (2013.01) | |
| *A61B 5/01* | (2006.01) | |
| *A61B 17/00* | (2006.01) | |
| *A61B 18/00* | (2006.01) | |
| *A61M 25/00* | (2006.01) | |

(52) U.S. Cl.
CPC .................. *A61M 25/10188* (2013.11); *A61M 2025/0002* (2013.01)

(56) References Cited

U.S. PATENT DOCUMENTS

| | | | |
|---|---|---|---|
| 6,416,523 B1* | 7/2002 | Lafontaine | A61B 17/320758 600/373 |
| 7,275,447 B2* | 10/2007 | Krivitski | A61B 5/0255 600/506 |
| 2003/0033004 A1* | 2/2003 | Ishii | A61L 31/16 623/1.15 |
| 2003/0149368 A1* | 8/2003 | Hennemann | A61B 5/053 600/483 |
| 2006/0178670 A1* | 8/2006 | Woloszko | A61B 18/1402 606/48 |
| 2008/0319462 A1* | 12/2008 | Montague | A61B 17/32075 606/159 |
| 2009/0270729 A1* | 10/2009 | Corbucci | A61B 5/0205 600/438 |

* cited by examiner

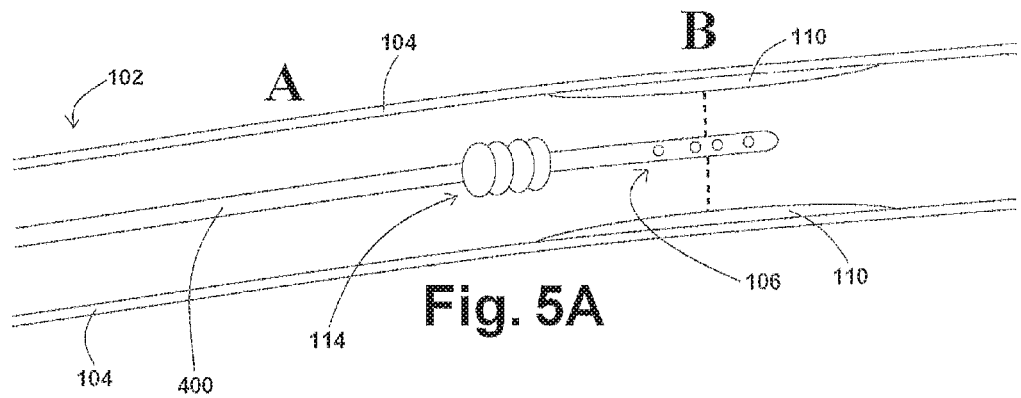
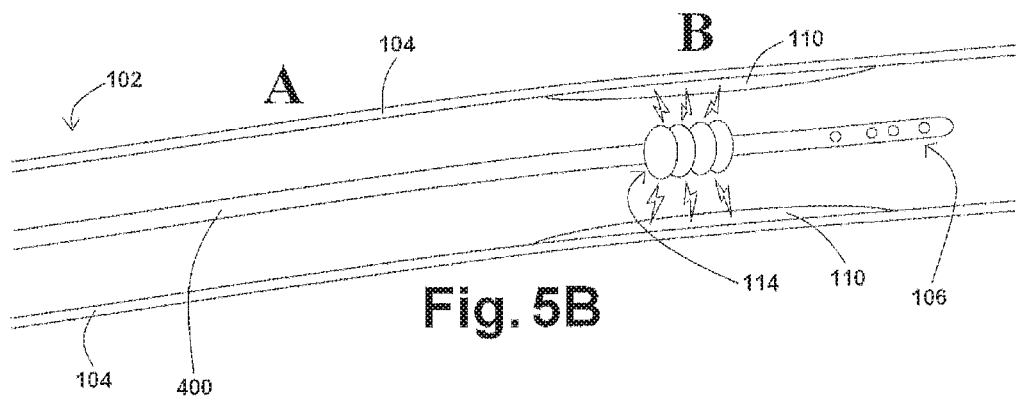
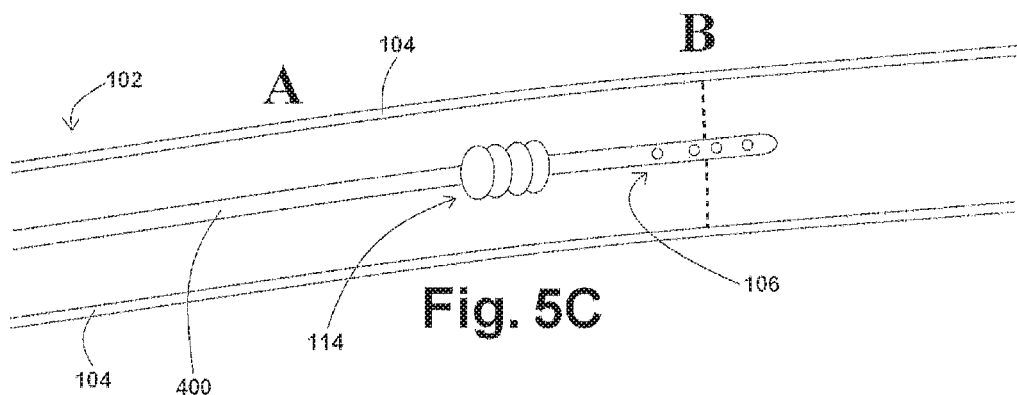

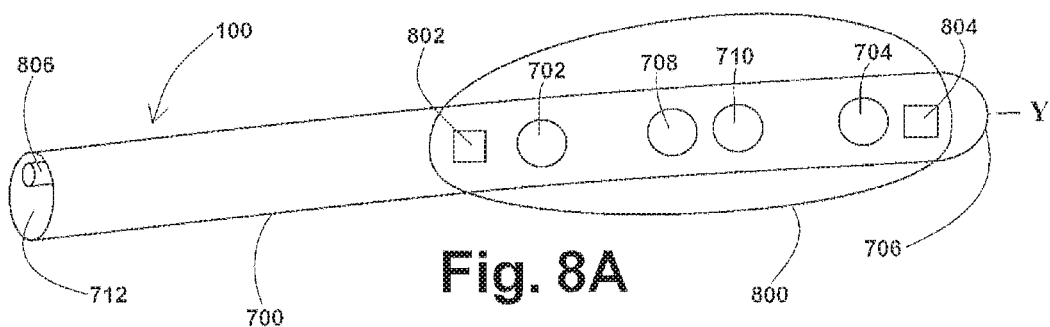
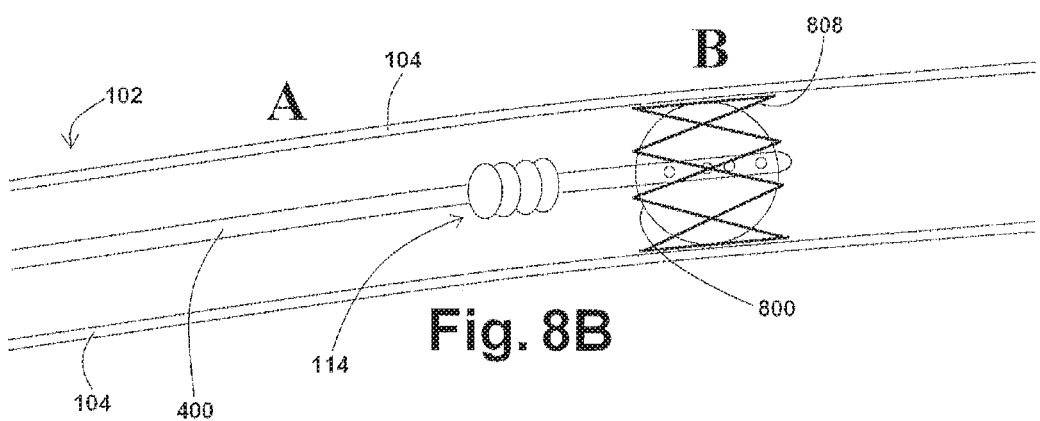
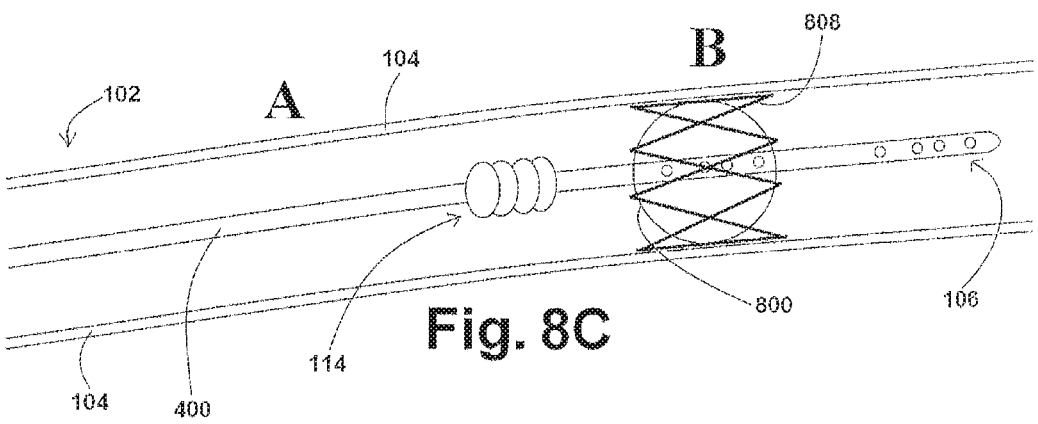

DEVICES, SYSTEMS, AND METHODS FOR REMOVING TARGETED LESIONS FROM VESSELS

PRIORITY

This U.S. nonprovisional application is related to, claims the priority benefit of, and is a U.S. continuation application of, U.S. patent application Ser. No. 12/748,166, filed Mar. 26, 2010 and issued as U.S. Pat. No. 9,603,545 on Mar. 28, 2017, which is related to, claims the priority benefit of, and is a U.S. continuation-in-part application of, U.S. patent application Ser. No. 12/428,656, filed Apr. 23, 2009 and issued as U.S. Pat. No. 8,465,452 on Jun. 18, 2013, which is related to, claims the priority benefit of, and is a U.S. continuation-in-part application of, U.S. patent application Ser. No. 12/098,242, filed Apr. 4, 2008 and issued as U.S. Pat. No. 8,078,274 on Dec. 13, 2011, which is related to, claims the priority benefit of, and is a U.S. continuation-in-part application of, U.S. patent application Ser. No. 11/891,981, filed Aug. 14, 2007 and issued as U.S. Pat. No. 8,114,143 on Feb. 14, 2012, which is related to, claims the priority benefit of, and is a U.S. divisional application of, U.S. patent application Ser. No. 10/782,149, filed Feb. 19, 2004 and issued as U.S. Pat. No. 7,454,244 on Nov. 18, 2008, which is related to, and claims the priority benefit of, U.S. patent application Ser. No. 60/449,266, filed Feb. 21, 2003, U.S. patent application Ser. No. 60/493,145, filed Aug. 7, 2003, and U.S. patent application Ser. No. 60/502,139, filed Sep. 11, 2003. The contents of each of these applications are hereby incorporated by reference in their entirety into this disclosure.

BACKGROUND

The disclosure of the present application relates generally to devices, systems, and methods for removing stenotic lesions from vessels. In at least one embodiment, the disclosure of the present application relates to methods for removing stenotic lesions from vessels involving obtaining one or more luminal size parameters of blood vessels, heart valves and other hollow visceral organs.

Coronary Heart Disease

Coronary heart disease is caused by atherosclerotic narrowing of the coronary arteries. It is likely to produce angina pectoris, heart attack or both. Coronary heart disease caused 466,101 deaths in USA in 1997 and is the single leading cause of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the STRESS trial, there was a significant difference in successful angiographic outcome in favor of stenting (96.1% vs. 89.6%), Aortic Stenosis Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.
Problems with Current Aortic Valve Area Measurements Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.
Other Viscera/Organs Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

As referenced in detail above, and given the prevalence of coronary heart disease and its potential severe prognosis, the availability of various devices, systems, and methods for removing stenotic lesions from vessels in an effective fashion would be well-received by the public, including treating physicians. The disclosure of the present application provides effective devices, systems, and methods useful to remove stenoic lesions and overcome known problems regarding current treatment devices and methods and the current lack of effective devices and methods to perform the same.

BRIEF SUMMARY

In at least one exemplary embodiment of a device for insertion within a luminal organ of the present disclosure, the device comprises an elongated body having a distal body end, and at least one directional sensor positioned along the elongated body at or near the distal body end, the at least one directional sensor capable of rotation about the elongated body. In another embodiment, the elongated body is selected from the group consisting of a catheter and a wire. In yet another embodiment, the elongated body is configured to fit within a lumen of a luminal organ.

In at least one exemplary embodiment of a device for insertion within a luminal organ of the present disclosure, the device further comprises a detector positioned along the elongated body at or near the distal body end, the detector capable of measuring a luminal size parameter when at least part of the elongated body is positioned within a lumen of a lumina organ. In an additional embodiment, the detector comprises a tetrapolar arrangement of electrodes. In another embodiment, the tetrapolar arrangement of electrodes comprises two detection electrodes positioned in between two excitation electrodes. In yet another embodiment, the at least one directional sensor is at least one electrode of the tetrapolar arrangement of electrodes. In an additional embodiment, the at least one directional sensor is independent of the tetrapolar arrangement of electrodes.

In at least one exemplary embodiment of a device for insertion within a luminal organ of the present disclosure, the at least one directional sensor is further capable of extending outward. from the elongated body. In another embodiment, when at least part of the elongated body is positioned within a lumen of a lumina organ, the at least one directional sensor is capable of extending outward from the elongated body to physically touch the luminal organ or a structure therein. In an additional embodiment, the at least one directional sensor is capable of obtaining a measurement from the luminal organ or the structure therein that the directional sensor is touching.

In at least one exemplary embodiment of a device for insertion within a luminal organ of the present disclosure, the at least one directional sensor is an impedance sensor, and wherein the measurement is an impedance measurement. In another embodiment, when a constant voltage is applied to the at least one directional sensor, the measurement is a current measurement indicative, of electrical impedance of the luminal organ or the structure therein that the directional sensor is touching. In yet another embodiment, when a constant current is applied to the at least one directional sensor, the measurement is a voltage measurement indicative of electrical impedance of the luminal organ or the structure therein that the directional sensor is touching. In an additional embodiment, the at least one directional sensor is a thermistor, and wherein the measurement is a temperature measurement.

In at least one exemplary embodiment of a device for insertion within a luminal organ of the present disclosure, the device further comprises an extension apparatus coupled to the at least one directional sensor, the extension apparatus capable of extending, the at least one directional sensor from a first position to an extended second position. In an additional embodiment, the extension apparatus is selected from the group consisting of a mechanical actuator, an electro-mechanical actuator, and a steering device. In various embodiments, the device further comprises a rotation apparatus coupled to a rotatable portion of the elongated body, the rotation apparatus capable of rotating the rotatable portion. In another embodiment, the rotation apparatus is selected from the group consisting of a mechanical actuator, an electro-mechanical actuator, and a steering device. In yet another embodiment, when the at least one directional sensor is positioned along the elongated body on the rotatable portion, the at least one directional sensor is capable of rotation by operation of the rotation apparatus. In an additional embodiment, the rotatable portion is capable of a full 360° rotation about the elongated body.

In at least one exemplary embodiment of a device for insertion within a luminal organ of the present disclosure, the at least one directional sensor is positioned at about 45 degrees to about 90 degrees of a circumference of the elongated body. In another embodiment, the device further comprises at least one treatment portion capable of removing at least part of a stenotic lesion from a luminal organ. In yet another embodiment, the at least one treatment portion is selected from the group consisting of a cutting balloon, a cryoplasty device, a rotational atherectomy device, a laser angioplasty device, a vibrating catheter, a vibrating blade, and a vibrating drill. In an additional embodiment, the device further comprises a detector comprising a tetrapolar arrangement of electrodes positioned along the device within a balloon, wherein the electrodes are operable to measure at least one luminal parameter within the balloon at one or more stages of balloon inflation.

In at least one exemplary embodiment of a device for insertion within a luminal organ of the present disclosure, the elongated body comprises a catheter having a suction/infusion port in communication with a lumen of the catheter, wherein the catheter is configured to facilitate one or more fluid injections into a lumen of a luminal organ when at least part of the elongated body is positioned therein. In an additional embodiment, the device further comprises at least one fluid delivery source operably coupled to the lumen of the catheter, whereby one or more fluids may be injected from the at least one fluid delivery source through the lumen of the catheter, through the suction/infusion port, and into the luminal of the luminal organ. In various embodiments, the device further comprises a current/voltage source in commmunication with one or more of the directional sensor and the tetrapolar arrangement of electrodes, the current/voltage source capable of supplying a constant current and/or a constant voltage thereto to facilitate one or more measurements indicative of electrical impedance of the luminal organ or a structure therein. In another embodiment, the device further comprises a data acquisition and processing system operably coupled to the device, the data acquisition and processing system capable of receiving the one or more measurements from the device and calculating at least one luminal size parameter and/or determining at least one luminal organ or structure type based upon the one or more measurements. In another embodiment, the device further comprises an inflatable balloon coupled to the elongated body, the inflatable balloon capable of inflation to place a stent positioned around the inflatable balloon within a lumen of a lumina organ.

In at least one embodiment of a device for insertion within a lumina organ of the present disclosure, the device comprises an elongated body having a distal body end, the elongated body configured to fit within a lumen of a luminal organ, at least one directional sensor positioned along the elongated body at or near the distal body end, the at least one directional sensor capable of rotation about the elongated body and further capable of extension outward from the elongated body to physically touch the luminal organ or a structure therein, the at least one directional sensor operable to obtain a measurement indicative of electrical impedance of the luminal organ or the structure therein that the directional sensor is touching, at least one detector positioned along the elongated body at or near the distal body end, the at least one detector capable of measuring a luminal size parameter when at least part of the elongated body is positioned within the lumen of the luminal organ, and at least one treatment portion capable of removing at least part of a stenotic lesion from the luminal organ.

In at least one embodiment of a device for removing a stenotic lesion from a vessel of the present disclosure, the device comprises at least one sizing portion capable of measuring a luminal size parameter when at least part of the device is positioned within a lumen of a luminal organ, at least one typing portion, wherein at least part of the at least one typing portion is capable of physically touching a portion of the luminal organ or a structure therein, and at least one treatment portion capable of removing at least part of a stenotic lesion from the luminal organ. In another embodiment, the at least one sizing portion comprises a tetrapolar arrangement of two detection electrodes positioned in between two excitation electrodes. In yet another embodiment, the at least one treatment portion is selected from the group consisting of a cutting balloon, a cryoplasty device, a rotational atherectomy device, a laser angioplasty device, a vibrating catheter, a vibrating blade, and a vibrating drill. In an additional embodiment, the at least one treatment portion comprises a balloon, and wherein the at least one sizing portion comprises at least one pressure sensor capable of detecting at least one pressure within the balloon at one or more stages of balloon inflation.

In at least one embodiment of a device for removing a stenotic lesion from a vessel of the present disclosure, the device further comprises at least one suction/infusion port in communication with at least one device lumen, the suction/infusion port operable to facilitate one or more fluid injections into the lumen of the luminal organ, and at least one fluid delivery source operably coupled to the at least device lumen, whereby one or more fluids may be injected from the at least one fluid delivery source through the at least one device lumen, through the at least one suction/infusion port, and into the lumen of the luminal organ. In another embodiment, the device further comprises a current source in communication with the two excitation electrodes, said current source operable to supply current to the two excitation electrodes to enable measurement of at least one conductance value, thereby enabling calculation of a luminal size parameter. In yet another embodiment, the device further comprises a data acquisition and processing system operably coupled to the device, the data acquisition and processing system operable to receive conductance data from the device to calculate at least one luminal parameter based upon said conductance data and to display the calculated at least one luminal parameter to facilitate operational control of the at least one treatment portion of the device.

In at least one embodiment of a system for removing a stenotic lesion of a vessel of the present disclosure, the system comprises a treatment device, the treatment device comprising at least one treatment portion capable of a removing at least part of a stenotic lesion from a luminal organ, and a sizing/typing device, the sizing/typing device comprising electrodes for measuring a first luminal size parameter when the typing/sizing device is positioned within a lumen of the luminal organ, and at least one directional sensor capable of physically touching a portion of the luminal organ or a structure therein to obtain a first vessel characteristic indicative of the luminal organ or the structure therein. In another embodiment, the treatment device comprises a catheter, and wherein the sizing/typing device comprises a wire selected from the group consisting of a guide wire, a pressure wire, and a flow wire.

In at least one embodiment of a method of removing at least part of a stenotic lesion within a luminal organ of the present disclosure, the method comprises the steps of (a) positioning at least part of a device within a luminal organ at a first location, (b) operating the device to obtain a first luminal size parameter and a first measurement indicative of electrical impedance of the luminal organ or a structure therein that at least part of the device is physically touching at the first location, (c) moving at least part of the device to a second location within the luminal organ, (d) operating the device to obtain a second luminal size parameter and a second measurement indicative of electrical impedance of the luminal organ or the structure therein that at least part of the device is physically touching at the second location, (e) determining whether or not a stenotic lesion is present at either the first location or the second location based on one or more of the first luminal size parameter, the first measurement, the second luminal size parameter, and the second measurement, (f) if the stenotic lesion is present, moving at least part of the device having a treatment portion to a stenotic lesion location, and (g) if the stenotic lesion is present, operating the treatment portion of the device to remove at least part of the stenotic lesion. In another embodiment, the method further comprises the steps of (h) measuring a then-current luminal size parameter at the stenotic lesion location, (i) comparing the then-current luminal size parameter to either the first luminal size parameter or the second luminal size parameter that is indicative of the stenotic lesion location, and (j) if the then-current luminal size parameter does not equal a preferred luminal size parameter, repeating steps (g), (h), and (i) until the then-current luminal size parameter equals or exceeds the preferred luminal size parameter.

In at least one embodiment of a method of removing at least part of a stenotic lesion within a luminal organ of the present disclosure, the preferred luminal size parameter is determined based upon the first luminal size parameter and the second luminal size parameter. In another embodiment, steps (b) and (d) are performed in the presence of a saline injection. In yet another embodiment, the step of moving at least part of the device to a second location comprises advancing or retracting at least part of the device within the luminal organ. In at least one embodiment, the step of moving at least part of the device to a second location comprises rotating at least part of the device within the luminal organ.

In at least one embodiment of a method of removing at least part of a stenotic lesion within a luminal organ of the present disclosure, the first luminal size parameter, the second luminal size parameter, and then-current luminal size parameter(s) are obtained using a detector coupled to the device. In another embodiment, the first measurement and the second measurement are obtained using a directional sensor coupled to the device. In yet another embodiment, the step of measuring then then-current luminal size parameter at the stenotic lesion location further comprises measuring a then-current measurement indicative of electrical impedance of the luminal organ or structure therein, and wherein the step of comparing the then-current luminal size parameter to either the first luminal size parameter or the second luminal size parameter further comprises comparing either the first measurement or the second measurement to the then-current measurement. In an additional embodiment, steps (g), (h), and (i) are repeated if the then-current luminal size parameter does not equal a preferred luminal size parameter or if the then-current measurement is indicative of electrical impedance of the stenotic lesion.

In at least one embodiment of a method of removing at least part of a stenotic lesion within a luminal organ of the present disclosure, the method further comprises the step of ceasing the operation of the treatment portion of the device when the then-current luminal size parameter equals or exceeds the preferred luminal size parameter. In another embodiment, the method further comprises the steps of selecting an appropriately-sized stent, and implanting the stent into the luminal organ.

In at least one embodiment of a method of removing at least part of a stenotic lesion within a luminal organ of the present disclosure, the method comprises the steps of positioning a device within a luminal organ, the device comprising at least one sizing portion, at least one typing portion, and at least one treatment portion, operating the at least one sizing portion of the device to obtain luminal size parameter data, operating the at least one sizing portion of the device to obtain type data indicative of electrical impedance of the luminal organ or a structure therein, and operating the at least one treatment portion at a location within the luminal organ at or near a stenotic lesion, whereby operation of the at least one treatment portion is based upon the luminal size parameter data and the type data, whereby operation of the at least one treatment portion removes at least part of the stenotic lesion. In another embodiment, the method further comprises the step of ceasing operation of the at least one treatment portion when the luminal size parameter data indicates a preferred luminal size parameter. In yet another embodiment, the method further comprises the step of ceasing operation of the at least one treatment portion when the type data is no longer indicative of electrical impedance of a stenotic lesion. In an additional embodiment, the steps of operating the at least one sizing portion and operating the at least one sizing portion are performed in the presence of a saline injection.

In at least one embodiment of a method of removing at least part of stenotic lesion within a luminal organ of the present disclosure, the method comprises the steps of (a) positioning a device within a luminal organ, the device comprising at least one typing portion and at least one treatment portion, (b) operating the at least one typing portion of the device to obtain initial type data indicative of electrical impedance of the luminal organ or a structure therein, (c) operating the at least one treatment portion if the type data is indicative of electrical impedance of a stenotic lesion to remove at least part of the stenotic lesion, and (d) operating the at least one typing portion of the device again to obtain then-current type data indicative of electrical impedance of the luminal or the structure therein, and (e) repeating steps (c) and (d) until the then-current type data does not indicate the presence of the stenotic lesion.

BRIEF DESCRIPTION OF THE DRAWINGS

FIGS. 4B, 5A, and 5C show cross-sectional views of a vessel wherein a sizing portion of the exemplary combination device is positioned at a second location within the vessel, according to the present disclosure;

FIGS. 4C and 5B show cross-sectional views of a vessel wherein a treatment portion of the exemplary combination device is positioned at a second location within the vessel and shown in operation, according to the present disclosure;

FIG. 8A shows an exemplary embodiment of a sizing device comprising a balloon coupled thereto, according to an embodiment of the present disclosure;

FIGS. 8B and 8C show exemplary embodiments of devices placing stents within a vessel, according to an embodiment of the present disclosure;

DETAILED DESCRIPTION

Figure 1A:
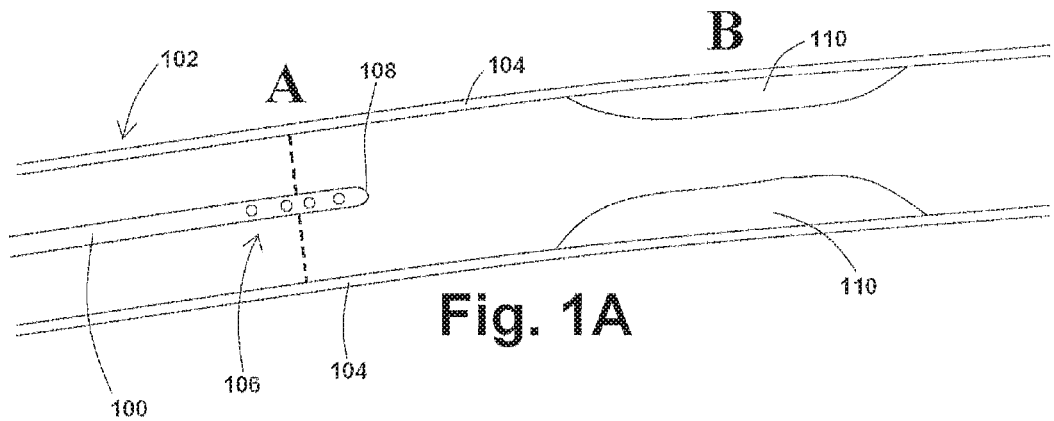
FIG. 1A shows a cross-sectional view of a vessel having a stenotic lesion and an exemplary sizing device positioned therein, according to an embodiment of the present disclosure.

Reference will now be made to the embodiments illustrated in the drawings and specific language will be used to describe the same. It will nevertheless be understood that no limitation of scope is intended by the description of these embodiments.

In at least one embodiment of a method for removing a stenotic lesion of a vessel, the method comprises the steps of measuring at least two luminal parameters, determining a preferred luminal size parameter, and operating a treatment device to increase at least one of the luminal parameters.

In at least one exemplary method for removing a stenotic lesion of a vessel, the method comprises the steps of measuring a first luminal size parameter at a first location within a vessel lumen, measuring a second luminal size parameter at a second location within the vessel lumen, determining a preferred second luminal size parameter based upon the first luminal size parameter and the second luminal size parameter, and positioning a treatment device at or near the second location. In at least one method, the method further comprises the steps of operating the treatment device to increase the second luminal size parameter and measuring a then-current luminal size parameter at the second location. After the then-current luminal size parameter at the second location is measured, an exemplary method for removing a stenotic lesion of a vessel comprises the step of comparing the then-current luminal size parameter to the preferred second luminal size parameter, and if the then-current luminal size parameter does not equal the preferred second luminal size parameter, an exemplary method comprises repeating the steps of operating the treatment device to increase the second luminal size parameter, measuring another then-current luminal size parameter at the second location, and comparing the then-current luminal size parameter to the preferred second luminal size parameter. In at least one embodiment of such a method, the aforementioned three steps (essentially a feedback loop) are repeated until the then-current luminal size parameter equals the preferred second luminal size parameter.

In various embodiments of methods of the disclosure of the present application, one or more luminal size parameters are measured. In at least one embodiment, the various luminal size parameters (the first luminal size parameter and the second luminal size parameter, for example) comprise luminal diameters. For example, and when performing an exemplary method of the disclosure of the present application to remove a vessel plaque (an exemplary stenotic lesion), a first luminal diameter may be measured at a location within the vessel, and second luminal diameter may be measured at a second location within the vessel. In another example, the luminal size parameters may comprise luminal cross-sectional areas. In yet another example, the luminal size parameters may comprise one or more other luminal geometric calculations, including, for example, a luminal circumference, each or all of which may share one or more similar calculated components (like a luminal diameter or a luminal radius, for example).

In an exemplary embodiment of a method for removing a stenotic lesion of a vessel of the disclosure of the present application, the first location comprises a location without a stenotic lesion, and the second location comprises a location with a stenotic lesion. Alternatively, and in another exemplary embodiment, the first location comprises a location with a relatively small stenotic lesion, and the second location comprises a location with relatively large stenotic lesion. In either embodiment, or as may be with other embodiments, the luminal size parameters at the first and second locations may vary from one another.

For example, and as shown in FIG. 1A, a sizing device 100 may be positioned within the lumen of a vessel 102 at a first location "A" as shown in the figure. Sizing device 100 may then operate to determine a first luminal size parameter at location "A", for example, as shown in FIG. 1A. As shown in the figure, the first luminal size parameter (as indicated by the dotted line extending from one vessel wall 104 to another) may comprise, for example, a luminal diameter or luminal cross-sectional area. In this exemplary embodiment, sizing device 100 comprises a sizing portion 106 located at or near the distal end 108 of sizing device 100. In such an embodiment, sizing portion 106 of sizing device 100 is the portion of sizing device 100 operable to obtain one or more luminal size parameters. In addition, and as shown in FIG. 1A, sizing portion 106 of sizing device 100 is positioned at a first location within the vessel that does not have a stenotic lesion 110.

Figure 1B:
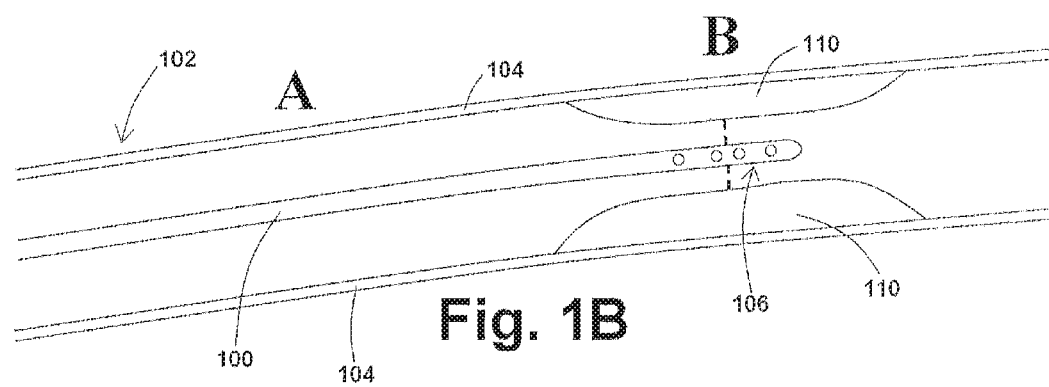
FIG. 1B shows the cross-sectional view of a vessel wherein the exemplary sizing device is positioned at a second location within the vessel, according to an embodiment of the present disclosure.

An exemplary embodiment of a sizing device 100 positioned within the lumen of a vessel 102 at a second location is shown in FIG. 1B. As shown in FIG. 1B, sizing device 100 may be introduced further within vessel 102 to a second location "B" as shown, wherein the second location is a location within vessel 102 having a stenotic lesion 110. In such an embodiment, and as shown in FIG. 1B, sizing device 100 may be operable to determine a second luminal size parameter (as indicated by the dotted line extending from sizing device 100 at second location "B"), noting that, for example, the second luminal size parameter may be relatively smaller than the first luminal size parameter if the second lumina size parameter is obtained at a portion within vessel 102 having a stenotic lesion 110. For example, sizing device 100 may obtain a first luminal diameter at location "A" and a second luminal diameter at location "B", and as shown in FIGS. 1A and 1B, the first luminal diameter would be larger than the second luminal diameter.

Figure 1C:
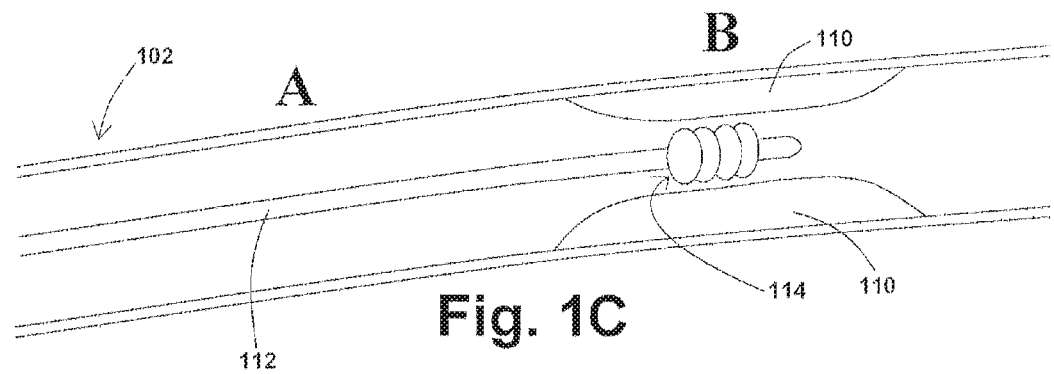
FIG. 1C shows a cross-sectional view of a vessel wherein an exemplary treatment device is positioned at a second location within the vessel, according to an embodiment of the present disclosure.
Figure 2A:
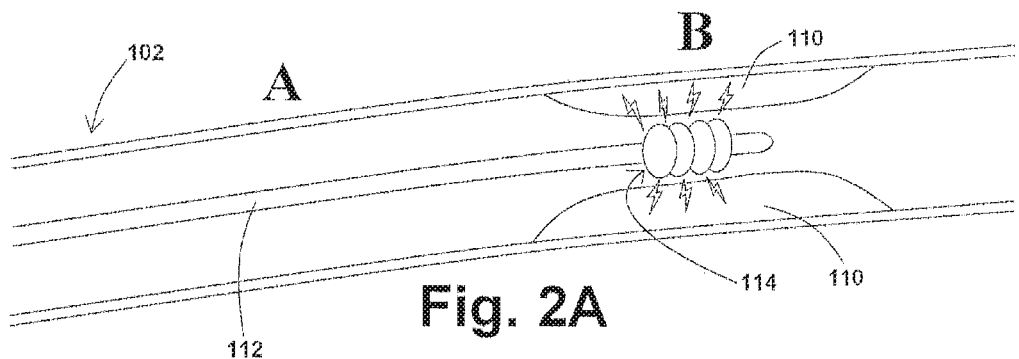
FIG. 2A shows an exemplary treatment device in operation, according to an embodiment of the present disclosure.

An exemplary embodiment of a method for removing a stenotic lesion of a vessel of the present application may comprise the step of positioning a treatment device within a vessel at or near at least one location within the vessel. As shown in FIG. 1C, a treatment device 112 is shown positioned within a lumen of a vessel 102, wherein at least one treatment portion 114 of treatment device 112 is positioned at or near a stenotic lesion 110 present within the lumen of vessel 102. Operation of treatment portion 114 of treatment device 112 is shown in FIG. 2A, with operation of the device indicated by the symbols above and below treatment portion 114. Said operation symbols are not intended to be limited to, for example, the application of electrical current—said symbols are intended merely to visually indicate operation of treatment portion 114 of treatment device 112.

Figure 2B:
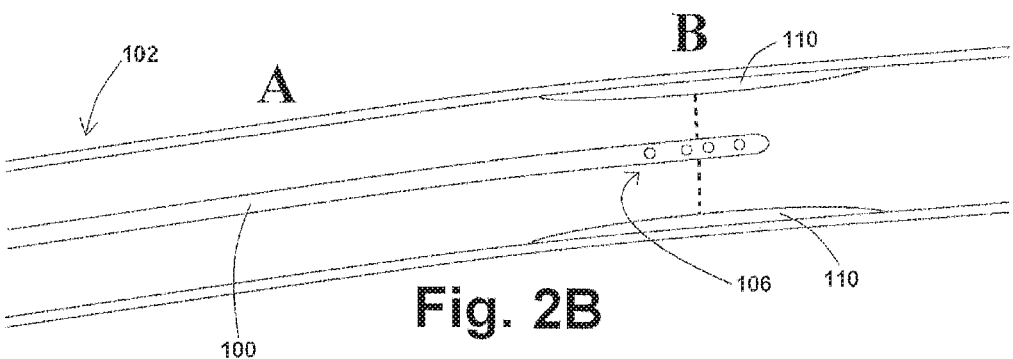
FIG. 2B shows the exemplary sizing device is positioned at a second location within the vessel obtaining a then-current luminal size parameter, according to an embodiment of the present disclosure.

After operation of treatment device 112 as shown in FIG. 2A, a determination as to the potential effectiveness of the treatment may be made by obtaining one or more luminal size parameters at the treatment site. As shown in FIG. 2B, sizing device 100 is present within the lumen of vessel 102, and is operable to obtain a then-current luminal size parameter (as indicated by the dotted line extending from sizing device 100 at second location "B"), which, as shown in the exemplary embodiment depicted in FIG. 2B, is relatively larger than the original second luminal size parameter. In this embodiment, a relatively large then-current luminal size parameter as compared to the original second luminal size parameter is indicative of at least a partially-successful stenotic lesion removal treatment, also as indicated by the smaller stenotic lesions 110 shown in FIG. 2B. A user may compare the then-current luminal size parameter to any number of other obtained luminal size parameters, including, but not limited to, the first luminal size parameter the second luminal size parameter, and a preferred second luminal size parameter, as described within example FIGS. 1A-2B and herein, as appropriate.

For example, and using numerical values merely as an example, if a first luminal size parameter is a vessel diameter of 0.7 mm, and a second luminal size parameter at a location within a vessel 102 having at least one stenotic lesion 110 is 0.2 mm in diameter, a user may select/determine a preferred second luminal size parameter of 0.5 mm in diameter, for example. Such a larger preferred second luminal size parameter relative to the original second luminal size parameter, when achieved based upon a stenotic lesion removal treatment, would be indicative of a partial removal of a stenotic lesion 110 from the vessel 102. A user may instead decide that a preferred second luminal size parameter is equivalent to the first luminal size parameter, which, as described in this particular example, would be indicative of total or near-total removal of a stenotic lesion 110 from a vessel 102 at the treatment site.

Figure 2C:
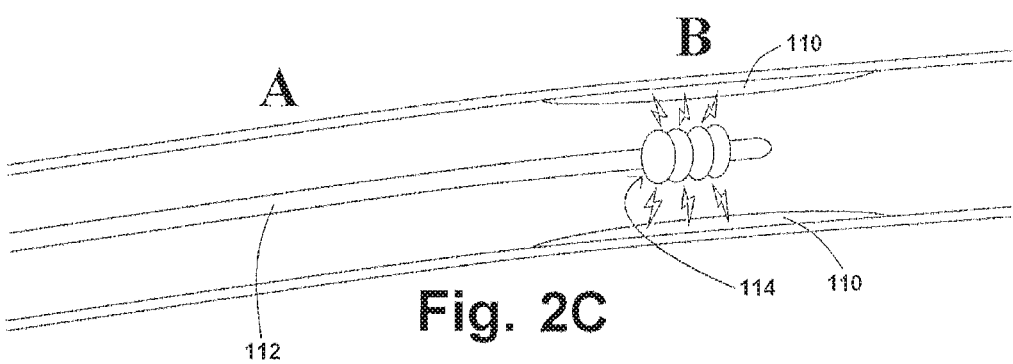
FIG. 2C shows the exemplary treatment device of FIGS. 1C and 2A in operation, according to an embodiment of the present disclosure.

As shown in FIG. 2C, treatment device 112 is shown re-inserted into the treatment site at or near stenotic lesion(s) 110, and is shown operating to potentially remove additional stenotic lesion(s) 110 from the treatment site. The scenario shown in FIG. 2C is indicative of a situation where a user has decided that the previously-measured then-current luminal sin parameter is not equal to or within a range of an acceptable/preferred second luminal size parameter, and that the user has decided to continue treatment using treatment device 112 in attempt to remove additional stenotic lesion(s) 110 from the treatment site.

Figure 3A:
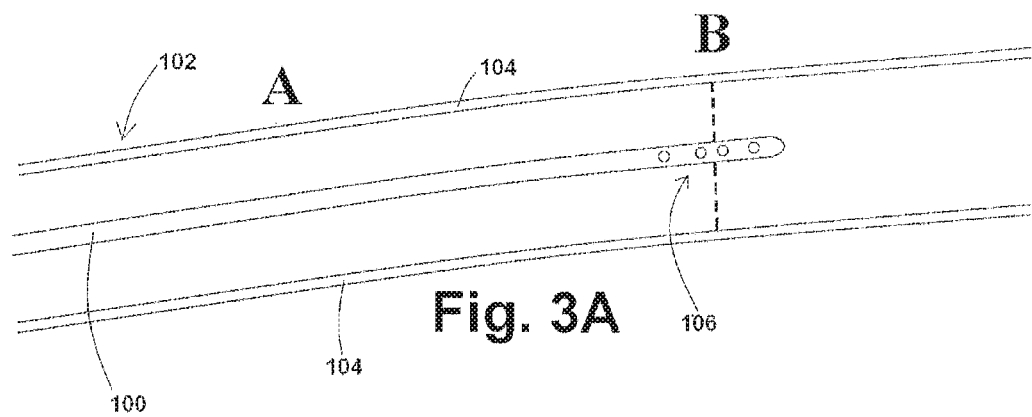
FIG. 3A shows the exemplary sizing device of FIG. 2B, for example, positioned at a second location within the vessel obtaining an additional then-current luminal size parameter, according to an embodiment of the present disclosure.

FIG. 3A shows at least a portion of a sizing device present within a vessel after completely successful treatment to remove one or more stenotic lesions. As shown in FIG. 3A, sizing device 100 is positioned within the lumen of vessel

102, whereby sizing portion 106 of sizing device 100 is positioned at or near the original second location (indicated by "B"). Sizing device 100 is shown operating to obtain a then-current luminal size parameter, and in this particular example, and assuming that the vessel has a constant diameter throughout the portion shown in FIG. 3A, the then-current luminal size parameter would equal the original first luminal size parameter, indicative of complete removal of a stenotic lesion at the treatment site. In such a situation, a user may decide to cease treatment (and thus cease operation of treatment device 112) as the then current luminal size parameter would equal to, or be within, a preferred luminal size parameter, assuming such a preferred luminal size parameter is equal to the original first luminal size parameter.

Figure 3B:
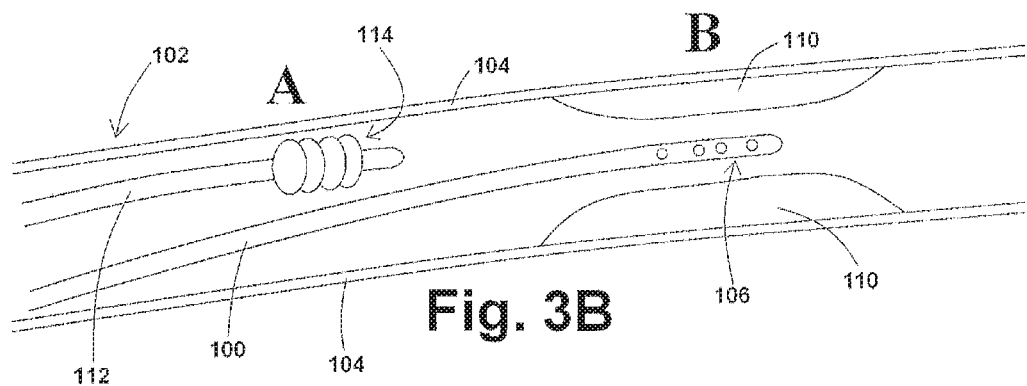
FIGS. 3B and 3C show a cross-sectional views of a vessel having an exemplary sizing device and an exemplary treatment device positioned therein, according to the present disclosure.
Figure 3C:
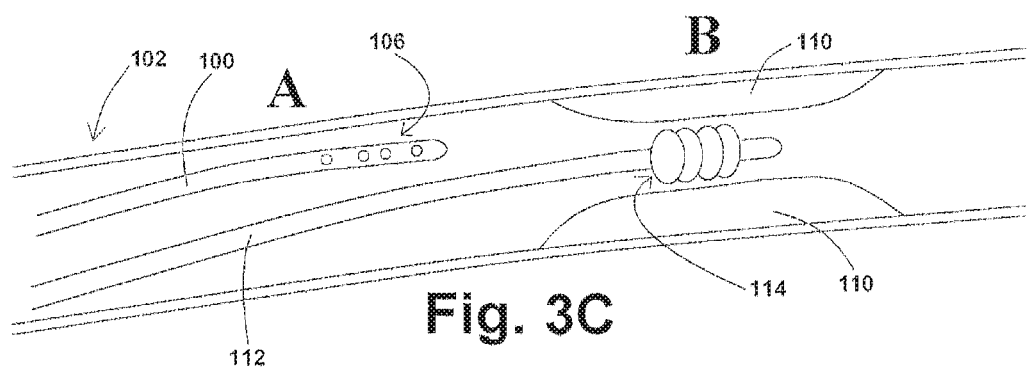

FIGS. 3B and 3C are indicative of situations where a user is using a sizing device and a treatment device, but does not completely remove one device from a vessel to use the other device. For example, and as shown in FIG. 3B, sizing portion 106 of sizing device 100 is shown positioned at or near stenotic lesion(s) 110, while at least a portion of treatment device 112 remains positioned within the lumen of vessel 102. Similarly, and as shown in FIG. 3C, treatment portion 114 of treatment device 112 is shown positioned at or near stenotic lesion(s) 110, while at least a portion of sizing device 100 remains positioned within the lumen of vessel 102.

Figure 4A:
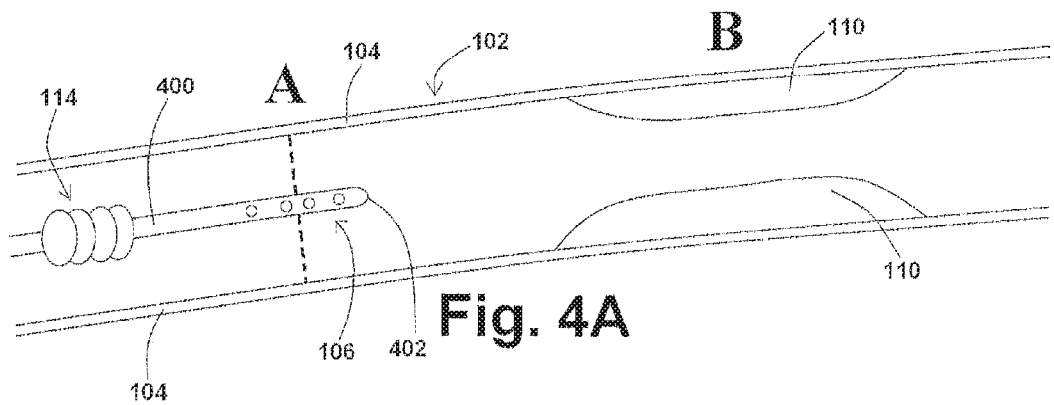
FIG. 4A shows a cross-sectional view of a vessel having a stenotic lesion and an exemplary combination device positioned therein, according to the present disclosure.
Figure 4B:
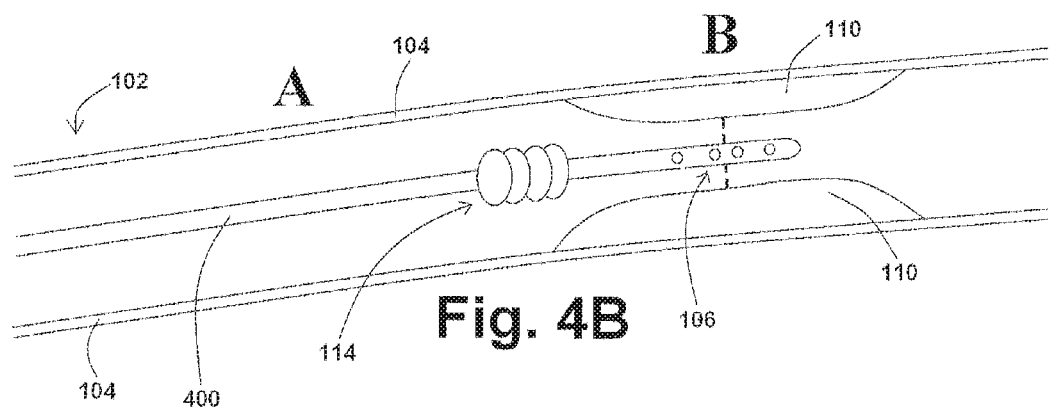
Figure 4C:
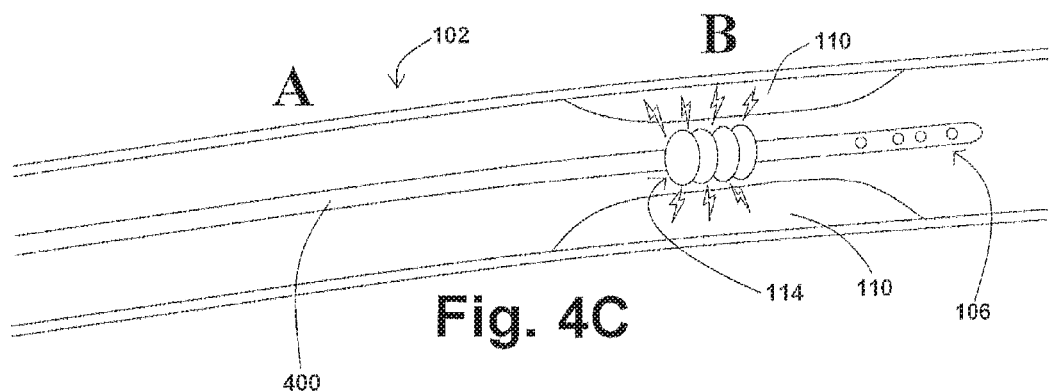

In at least an additional embodiment of a device of the disclosure of the present application, said device comprises at least one feature indicative of a sizing device and at least one feature indicative of a treatment device. For example, and as shown in FIGS. 4A-4C, an exemplary combination device 400 comprises a sizing portion 106 located at or near the distal end of combination device 400. In addition, and as shown in the exemplary embodiments shown in FIGS. 4A-4C, an exemplary combination device 400 also comprises a treatment portion 114 positioned along combination device. As referenced within the present application, an exemplary combination device 400 may be substantially equivalent, if not completely equivalent, to an exemplary sizing device 100 of the present application comprising at least one treatment portion 114, and similarly, an exemplary combination, device 400 may be substantially equivalent, if not completely equivalent, to an exemplary treatment device 112 comprising at least one sizing portion 106.

As shown in FIG. 4A, an exemplary combination device 400 is shown positioned within the lumen of a vessel 102, whereby sizing portion 106 of combination device 400 is positioned at or near a first location within vessel 102 (as indicated by "A"). Combination device 400 may then operate to determine a first luminal size parameter at location "A", for example, as shown in FIG. 4A. As shown in the figure, the first luminal size parameter (as indicated by the dotted line extending from one vessel wall 104 to another) may comprise, for example, a luminal diameter or luminal cross-sectional area. In this exemplary embodiment, combination device 400 comprises a sizing portion 106 located at or near the distal end 402 of sizing device 400. In such an embodiment, sizing portion 106 of combination device 400 is the portion of combination device 400 operable to obtain one or more luminal size parameters. In addition, and as shown in FIG. 4A, sizing-portion 106 of combination device 400 is positioned at a first location within the vessel that does not have a stenotic lesion 110.

An exemplary embodiment of a combination device 400 positioned within the lumen of a blood vessel 102 at a second location is shown in FIG. 4B. As shown in FIG. 4B, combination device 400 may be introduced further within vessel 102 to a second location "B" as shown, wherein the second location is a location within vessel 102 having a stenotic lesion 110. In such an embodiment, and as shown in FIG. 4B, combination device 400 may be operable to determine a second luminal size parameter (as indicated by the dotted line extending from combination device 400 at second location "B"), noting that, for example, the second luminal size parameter may be relatively smaller than the first luminal size parameter if the second luminal size parameter is obtained at a portion within vessel 102 having a stenotic lesion 110. For example, combination device 400 may obtain a first luminal diameter at location "A" and a second luminal diameter at location "B", and the first luminal diameter would be larger than the second luminal diameter.

An exemplary embodiment of a method for removing a stenotic lesion of a vessel of the present application may comprise the step of positioning a combination/treatment device within a vessel at or near at least one location within the vessel. As shown in FIG. 4C, combination device 400 is shown positioned within a lumen of a vessel 102, wherein at least one treatment portion 114 of combination device 400 is positioned at or near a stenotic lesion 110 present within the lumen of vessel 102. Operation of treatment portion 114 of combination device 400 is also shown in FIG. 4C, with operation of the device indicated by the symbols above and below treatment portion 114. As referenced above in connection with the operation of an exemplary treatment device 112, said operation symbols are not intended to be limited to, for example, the application of electrical current—said symbols are intended merely to visually indicate operation of treatment portion 114 of combination device 400.

As shown in FIG. 5A, combination device 400 is re-positioned within the lumen of vessel 102, and is operable to obtain a then-current luminal size parameter (as indicated by the dotted line extending from combination device 400 at second location "B"), which, as shown in the exemplary embodiment depicted in FIG. 5A, is relatively larger than the original second luminal size parameter. In this embodiment, a relatively large then-current luminal size parameter as compared to the original second luminal size parameter is indicative of at least a partially-successful treatment, also as indicated by the smaller stenotic lesions 110 shown in FIG. 5A. A user may compare the then-current luminal size parameter to any number of other obtained luminal size parameters, including, but not limited to, the first luminal size parameter the second luminal size parameter, and a preferred second luminal size parameter, as described within example FIGS. 4A-5A and herein, as appropriate.

As shown in FIG. 5B, combination device 400 is shown re-positioned within vessel 102 so that treatment portion 114 is positioned at or near stenotic lesion(s) 110, and is shown operating to potentially remove additional stenotic lesion(s) 110 from the treatment site. The scenario shown in FIG. 5B is indicative of a situation where a user has decided that the previously-measured then-current luminal size parameter is not equal to or within a range of an acceptable/preferred second luminal size parameter, and that the user has decided to continue treatment using treatment portion 114 of combination device 400 in attempt to remove additional stenotic lesion(s) 110 from the treatment site.

FIG. 5C shows at least a portion of a combination device 400 present within a vessel after completely successful treatment to remove one or more stenotic lesions. As shown in FIG. 5C, combination device 400 is re-positioned within the lumen of vessel 102, whereby sizing portion 106 of combination device 400 is positioned at or near the original second location (indicated by "B"). Combination device 400 is shown operating to obtain a then-current luminal size parameter, and in this particular example, and assuming that the vessel has a constant diameter throughout the portion shown in FIG. 5C, the then-current luminal size parameter would equal the original first luminal size parameter, indicative of complete removal of a stenotic lesion at the treatment site. In such a situation, a user may decide to cease treatment, (and thus cease operation of treatment device 112) as the then-current luminal size parameter would equal to, or be within, a preferred luminal size parameter, assuming such a preferred luminal size parameter is equal to the original first luminal size parameter.

In at least one embodiment of a treatment portion 114 of the present application, treatment portion 114 comprises a treatment portion selected from the group consisting of a cutting balloon, a cryoplasty device, a rotational atherectomy device, a laser angioplasty device, a vibrating catheter, a vibrating blade, and a vibrating drill. A common feature shared among these various treatment portion 114 compositions is that each one is operable to remove at least a portion of a stenotic lesion 110 from a vessel or luminal organ. As such, a number of other treatment portion 114 compositions either known or developed in the art may be useful in connection with the present disclosure so long as it is operable to remove at least a portion of a stenotic lesion 110 from a vessel or luminal organ. As referenced herein, the term "vessel" is intended to encompass any number of luminal organs, including blood vessels, present within an body.

Figure 6A:
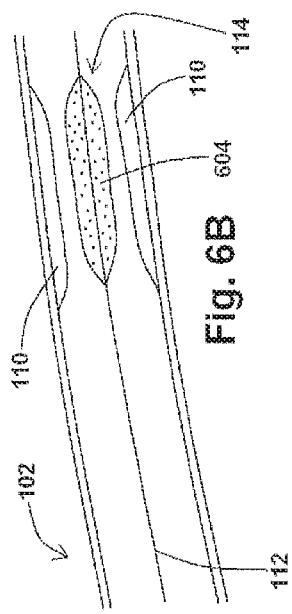
FIGS. 6A-6F show various embodiments of exemplary treatment portions of treatment devices, according to the present disclosure.

FIGS. 6A-6F show various embodiments of at least part of various treatment portions 114 of exemplary treatment devices 112 of the present disclosure. FIG. 6A shows an exemplary treatment device 112 of the present disclosure positioned within a vessel 102, wherein said treatment device 112 comprises a treatment portion 114 comprising a cutting balloon 600. Cutting balloon 600, as shown in FIG. 6A, may comprise one or more cutting portions 602, said cutting portions 602 operable to physically cut a stenotic lesion 110 within a vessel 102. In at least one embodiment, cutting balloon 600 may be inflated within the lumen of a vessel 102, whereby the inflation of cutting balloon 600 allows cutting portions 602 to engage and cut a stenotic lesion 110.

Figure 6B:
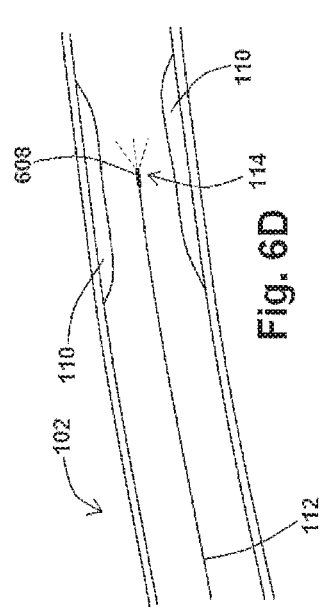

Another embodiment of a treatment portion 114 of a treatment device 112 of the present disclosure is shown in FIG. 6B. As shown in FIG. 6B, treatment portion 114 comprises a cryo-balloon 604 (an exemplary cryoplasty device) capable of inflation using a relatively cold gas and/or fluid such as nitrous oxide. Inflation of cryo-balloon 604 using a cold gas and/or fluid locally reduces the temperature within a vessel 102, providing potential benefits of being able to crack and/or remove a stenotic lesion 110 within said vessel 602 using such a cryoplasty device.

Figure 6C:
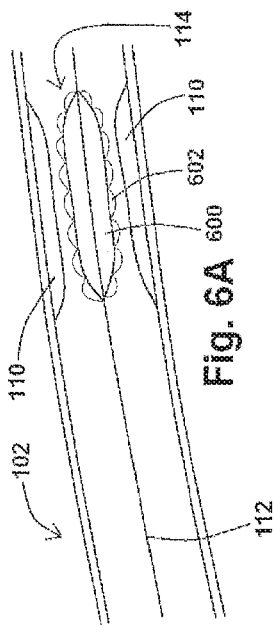

An additional embodiment of an exemplary treatment device 112 of the present application is shown in FIG. 6C. As shown in FIG. 6C, treatment device 112 comprises a rotational atherectomy device 606, whereby rotation of rotational atherectomy device 606 operates to cut a stenotic lesion 110 positioned within a vessel 102.

Figure 6D:
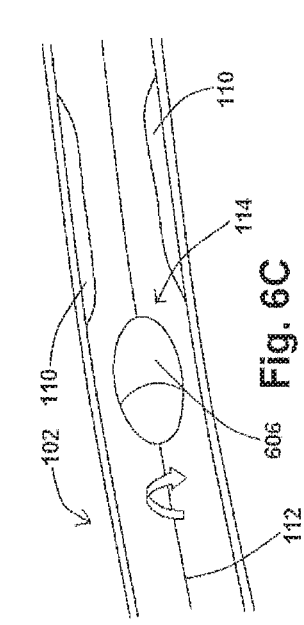

FIG. 6D Shows an embodiment of a treatment portion 114 of a treatment device 112 comprising a laser angioplasty device 608. As shown in FIG. 6D, laser angioplasty device 608 may be positioned at the distal end of treatment device 112, and is operable to emit one or more beams of light (lasers) capable of disintegrating some or all of a stenotic lesion 110.

Figure 6E:
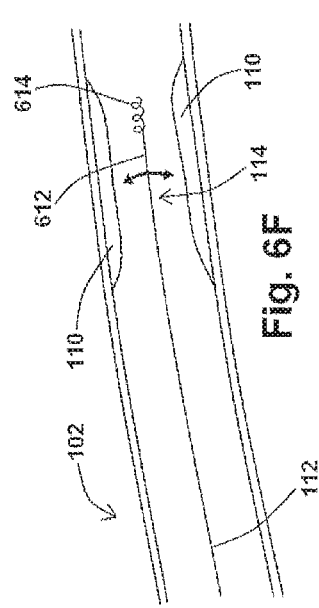
Figure 6F:
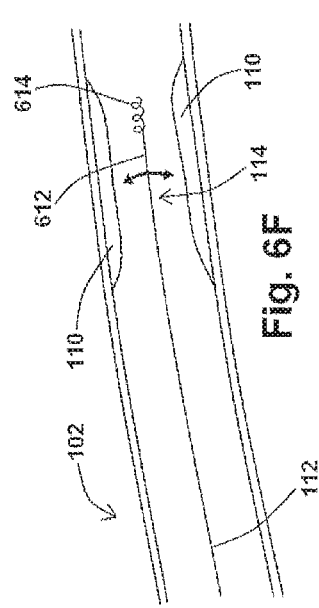

Additional embodiments of treatment portions 114 of exemplary treatment devices 112 of the disclosure of the present application are shown in FIGS. 6E and 6F. As shown in FIG. 6E, treatment portion 114 comprises a vibrating catheter 610 capable of vibration, for example, in the directions shown by the arrow in the figure. Vibrating catheter 610, when in operation, may physically remove some or all of a stenotic lesion 110 impacted by vibrating catheter 610. As shown in FIG. 6E, treatment portion 114 may comprise a vibrating drill 612, whereby vibrating drill 612 may operate similarly to vibrating catheter 610 as described above, and may be further operable to drill through a stenotic lesion 110 using drill tip 614.

The exemplary embodiments of treatment devices 114 shown in FIGS. 6A-6F and described herein are not intended to be an exhaustive list and/or description of treatment devices 112 of the present application, as one or more additional treatment devices 114 known in the art may be useful in one or more devices, systems, and/or methods of the present application.

Figure 7A:
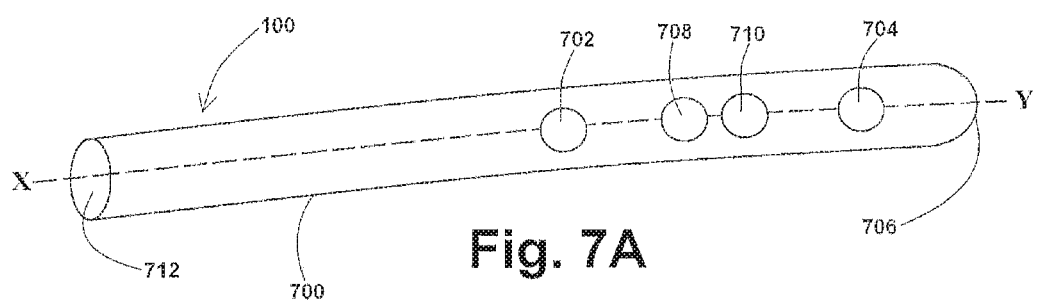
FIGS. 7A, 7B, and 7C show at least a portion of exemplary embodiments of sizing devices, according to the present disclosure.

As shown in FIGS. 1A and 1B, for example, a sizing device 100 is used to determine the various luminal size parameters. In at least one embodiment of at least a portion of sizing device 100, and as shown in FIG. 7A, sizing device 100 may comprise an elongated body 700 having a longitudinal axis extending from a proximal end to a distal end (as indicated by the dotted line extending from "X" to "Y" as shown in FIG. 5A). An exemplary sizing device 100 of the present disclosure may also comprise a first excitation electrode 702 and a second excitation electrode 704 positioned along the longitudinal axis of the elongated body 700 at or near a distal end 706 of the elongated body 700, and may further comprise a first detection electrode 708 and a second detection electrode 710 positioned along the longitudinal axis of the elongated body 700 in between the first excitation electrode 702 and the second excitation electrode 704. In at least one exemplary embodiment of a sizing device 100, the elongated body 700 comprises a catheter having a lumen extending along the longitudinal axis of the catheter. Furthermore, other sizing portions 106 not specifically disclosed herein but insertable within a vessel and operable to determine at least one luminal size parameter may comprise and/or be used within an exemplary device, system, and/or method of the present disclosure.

In at least one embodiment, operation of sizing device 100, sizing portion 106 of sizing device 100, or a sizing portion 106 of another device and/or system of the present disclosure, including technical operation of one or more electrodes disclosed herein to determine one or more luminal size parameters, is performed as disclosed within one or more of the patents and/or patent applications incorporated by reference herein, including, but not limited to, the disclosure of U.S. Pat. No. 7,454,244. For example, and with reference to an exemplary embodiment of a sizing portion 106 disclosed herein comprising electrodes as referenced herein, conductance of current flow through an organ lumen and organ wall and surrounding tissue is parallel; i.e., $$G(z, t) = \frac{CSA(z, t) \cdot C_b}{L} + G_p(z, t) \qquad [1a]$$

where $G_p(z,t)$ is the effective conductance of the structure outside the bodily fluid (organ wall and surrounding tissue) at a given position, z, along the long axis of the organ at a given time, t, and $C_b$ is the electrical conductivity of the bodily fluid which for blood generally depends on the temperature, hematocrit and orientation and deformation of blood cells, and L is the distance between the detection electrodes of sizing portion 106. Furthermore, Equation [1a] can be rearranged to solve for an exemplary luminal size parameter, namely cross sectional area CSA (t) with a correction factor, α, if the electric field is non-homogeneous, as $$CSA(z, t) = \frac{L}{\alpha C_b}[G(z, t) - G_p(z, t)] \quad [1b]$$

where α would be equal to 1 if the field were completely homogeneous. The parallel conductance, $G_p$, is an offset error that results from current leakage.

Figure 7B:
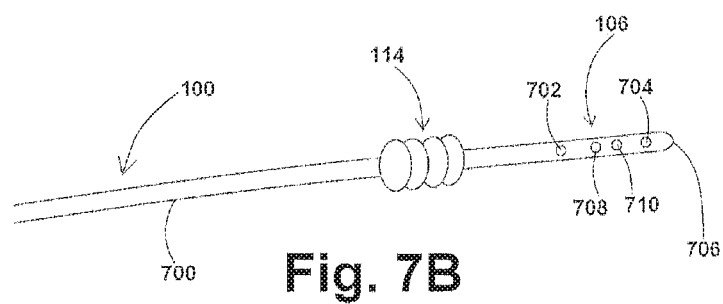
Figure 7C:
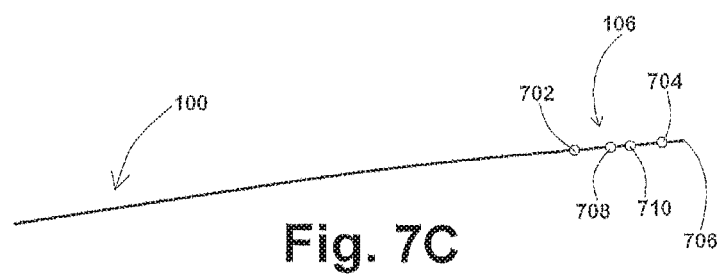

FIG. 7B shows an exemplary embodiment of a sizing device 100 comprising both a treatment portion 114 and a sizing portion 106. As shown in this exemplary embodiment, sizing portion 106 of device 100 comprises a first excitation electrode 702 and a second excitation electrode 704 positioned along elongated body 700 at or near a distal end 706 of the elongated body 700, and further comprises a first detection electrode 708 and a second detection electrode 710 positioned along the elongated body 700 in between the first excitation electrode 702 and the second excitation electrode 704. In this exemplary embodiment, sizing device 100, comprising both a treatment portion 114 and a sizing portion 106, may be substantially equivalent, if not completely equivalent, to an exemplary combination device 400 of the present application An additional exemplary embodiment of a sizing device 100 of the disclosure of the present application is shown in FIG. 7C. As shown in FIG. 7C, sizing device 100 comprises a wire having a first excitation electrode 702, a second excitation electrode 704, a first detection electrode 708, and a second detection electrode 710 positioned along the wire at or near the distal end 706 of sizing device 100.

Exemplary sizing devices 100 of the disclosure of the present application, as referenced herein, are operable to measure various luminal size parameters. In at least one embodiment wherein the elongated body of the sizing device 100 or treatment device 112 comprises a catheter having a lumen extending along the longitudinal axis of the catheter, an exemplary method for removing a stenotic lesion of a vessel of the present application comprises the step of measuring a first luminal size parameter which comprises the steps of providing electrical current flow to the first location through the catheter, injecting a first solution of a first compound having a first conductivity into the vessel lumen at the first location through the catheter, and measuring a first conductance value at the first location. An exemplary method may further comprise the steps of injecting a second solution of a second compound having a second conductivity into the vessel lumen at the first location through the catheter, measuring a second conductance value at the first location, and calculating a first luminal size paratheter based on the first conductance value, the second conductance value, the first conductivity of the first solution, and the second conductivity of the second solution. Such a method could be used to measure a second and/or subsequent luminal size parameter; noting that the location of the measuring of the conductance values may vary accordingly (for example, at a second location).

For example, and as referenced within priority U.S. Pat. No. 7,454,244 incorporated by reference in its entirety herein, at any given position, z, along the long axis of organ; vessel and at any given time, t, in the cardiac cycle, $G_p$ is a constant. Hence, two injections of different concentrations and/or conductivities of an NaCl solution give rise to two equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L\frac{[G_2(z, t) - G_1(z, t)]}{[C_2 - C_1]} \quad [4]$$

and $$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

In an exemplary embodiment of method for removing a stenotic lesion of a vessel of the present application, a sizing device 100 useful to measure the various luminal size parameters comprises a wire (as shown in FIG. 7C), and the treatment device 112 operable to increase at least one luminal size parameter comprises a catheter comprising at least one treatment portion 114. In at least one embodiment, the wire comprises a first excitation electrode 702 and a second excitation electrode 704 positioned along sizing device 100, and further comprises a first detection electrode 708 and a second detection electrode 710 positioned along sizing device 100 in between the first excitation electrode 702 and the second excitation electrode 704.

In another exemplary embodiment of a sizing device 100, sizing device 100 may comprise a guide wire, wherein such a guide wire may be positioned at least partially within a lumen of the catheter to guide the catheter within a vessel and to perform at least one method step of an exemplary method of the present disclosure.

In an exemplary embodiment of a treatment device 112 of the disclosure of the present application, treatment device 112 comprises at least one treatment portion 114 and at east one sizing portion 106. In at least one embodiment, the treatment portion 114 of treatment device 112 is operable to remove at least part of a stenotic lesion. In various embodiments, an exemplary treatment portion 114 of treatment device 112 (or a sizing device 100 or a combination device 400) may comprises a cutting balloon, a cryoplasty device, a rotational atherectomy device, a laser angioplasty device, a vibrating catheter, a vibrating blade, and a vibrating drill, exemplary embodiments of each of the same as shown in FIGS. 6A-6F and described herein.

In at least one embodiment of an exemplary sizing portion 106 of one or more devices of the present disclosure, sizing portion 106 comprises a first excitation electrode 702 and a second excitation electrode 704 positioned along the device, and further comprises a first detection electrode 708 and a second detection electrode 710 positioned along the device in between the first excitation electrode 702 and the second excitation electrode 704. In another embodiment wherein an exemplary treatment portion 114 comprises a balloon 800 (as shown, for example, in FIG. 8A, discussed below), the sizing portion 106 of an exemplary device of the disclosure of the present application may comprises the same or similar configuration of electrodes. For example, and in at least one embodiment, first excitation electrode 702, second excitation electrode 704, first detection electrode 708, and second detection electrode 710 may each be positioned along a treatment device 112 within balloon 800, and wherein the then-current luminal size parameter comprises a parameter measured within balloon 800 at one or more stages of balloon 800 inflation.

In at least an additional embodiment of an exemplary device of the present application, the device comprises an exemplary treatment portion. 114 comprising a balloon 800, and further comprises an exemplary sizing portion 106 comprising at least one pressure sensor 802. As shown in FIG. 8A, an exemplary sizing device 100 comprises balloon 800 surrounding the various electrodes positioned along the elongated body 700 of sizing device 100. In an exemplary embodiment, pressure sensor 802 is operable to detect at least one pressure within balloon 800 at one or more stages of balloon 800 inflation. As shown in FIG. 8A, balloon 800 may inflate and/or deflate via inflation/deflation port 804, allowing a gas and/or a liquid to be introduced into or removed from balloon 800 via suction/infusion tube 806.

As described herein, a user of one or more devices comprising at least one treatment portion 114 may, at some point, decide to stop operating treatment portion 114. The decision to stop may be for any number of reasons, including, but not limited to, achieving a preferred luminal size parameter based upon operation of treatment portion 114 on a stenotic lesion 110 within a vessel. In at least one embodiment of an exemplary method for removing a stenotic lesion of a vessel of the present disclosure, the method further comprises the step of ceasing operation of the treatment device 112 (or the treatment portion 114 of a device of the disclosure of the present application) when the then-current luminal size parameter equals the preferred second luminal size parameter. In at least one embodiment, the preferred second luminal size parameter is equal to the first luminal size parameter. In another embodiment, the preferred luminal size parameter comprises a preferred second luminal size parameter range.

In an exemplary embodiment of a method for removing a stenotic lesion of the present disclosure, the step of comparing the then-current luminal size parameter to the preferred second luminal size parameter comprises comparing the then-current luminal size parameter to the preferred second luminal size parameter range. In such a situation, and instead of a specific numerical size parameter target, the preferred luminal size parameter comprises a range of acceptable values. In an exemplary embodiment, a method for removing a stenotic lesion may comprise the step of ceasing the operation of treatment device 112 (or the treatment portion 114 of a device of the disclosure of the present application) when the then-current luminal size parameter is within the preferred second luminal size parameter range.

In at least one method for removing a stenotic lesion of the disclosure of the present application, the method further comprises the steps of selecting an appropriately-sized stent and implanting the stent into the vessel lumen. As shown in FIG. 8B, an exemplary device of the present application (shown as combination device 400) comprises a balloon 800 coupled thereto, and is shown in an inflated state while positioning a stent 808 within the lumen of a vessel 102. In another embodiment, and as shown in FIG. 8C, combination device 400 is shown performing a similar operation, noting that in this exemplary embodiment, combination device comprises a treatment portion 114, a sizing portion 106, and a balloon 800 positioned around various electrodes.

In at least one method for removing a stenotic lesion of the disclosure of the present application, the method further comprises the steps of obtaining at least one additional luminal size parameter between the first position and the second position, and constructing a lumen profile based upon the second luminal size parameter and the at least one additional luminal size parameter. In such a situation, multiple luminal size parameters may be used to construct a visual profile of changes in luminal size parameter over time and/or during treatment. In an exemplary method, multiple luminal size parameters are taken at various locations, allowing for the determination of a length of a stenotic lesion to be made based upon the lumen profile.

Figure 9A:
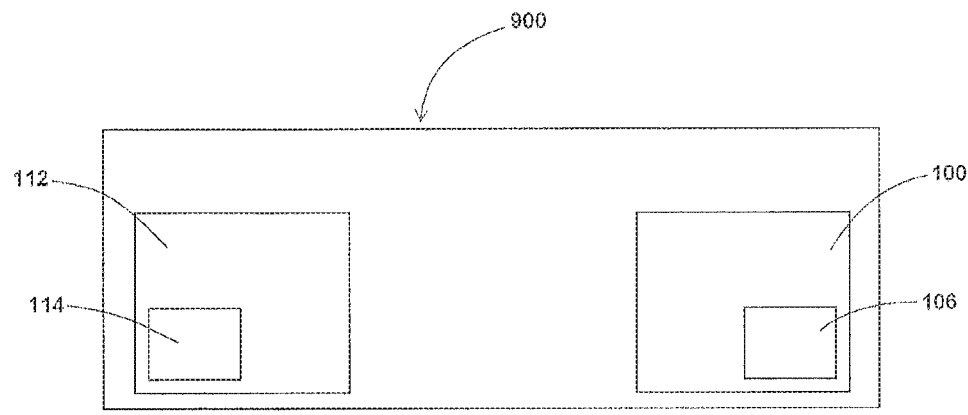
FIGS. 9A and 9B show exemplary embodiments of systems useful for removing stenotic lesions from vessels, according to the present disclosure.

In at least one embodiment of a system for removing a stenotic lesion of a vessel as shown in FIG. 9A, system 900 comprises a treatment device 112 and a sizing device 100. As referenced herein, and as shown in FIG. 9A, treatment device 112 may comprise at least one treatment portion 114 operable to remove at least part of a stenotic lesion 110, and an exemplary sizing device 100 may comprise at least one sizing portion 106 (including various electrodes, for example) operable to measure a first luminal size parameter when sizing device 100 is positioned at a first location, and further operable to measure a second luminal size parameter when sizing device 100 is positioned at a second location.

Any or all of the characteristics, features, elements, and/or limitations of the various devices referenced herein in connection with the above-referenced methods may apply to one or more exemplary systems of the present application. For example, and in an exemplary system 900, treatment device 112 may comprise a catheter, and sizing device 100 may comprises a wire selected from the group consisting of a guide wire, a pressure wire, and a flow wire. Said wire, when in use, may be positioned at least partially within a lumen of the catheter.

Figure 9B:
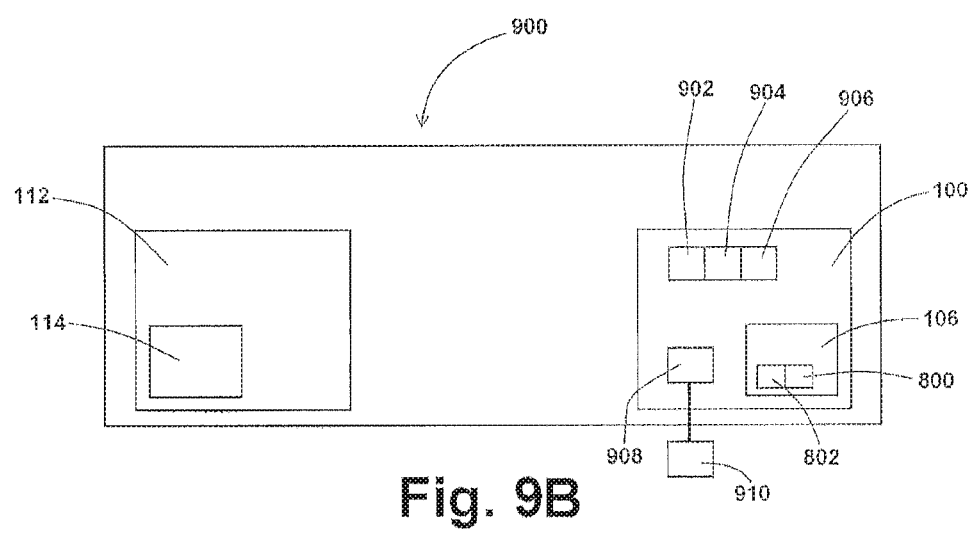

As shown in FIG. 9B, and in at least one embodiment of a system 900 for removing a stenotic lesion of a vessel of the present disclosure, treatment portion 114 of treatment device 112 comprises balloon 800, and sizing portion 106 of sizing device 100 comprises at least one pressure sensor 802. In such an embodiment, pressure sensor 802 may be operable to detect at least one pressure within balloon 800 at one or more stages of balloon inflation. In addition, and in an exemplary embodiment, pressure sensor 802 may be operable to measure a first pressure gradient and calculate at least one luminal parameter within balloon 800 based in part upon the first pressure gradient.

In at least one embodiment of a system for removing a stenotic lesion of a vessel, and as shown in FIG. 9B, system 900 further comprises at least one suction/infusion port 902 in communication with at least one lumen 904 of sizing device 100, said suction infusion port 902 operable to facilitate one or more fluid injections into a treatment site. In another embodiment, and as shown in FIG. 9B, system 900 may further comprise at least one fluid delivery source 906 operably coupled to lumen 904 of sizing device 100, whereby one or more fluids may be injected from fluid delivery source 906 through lumen 904 of sizing device 100, through suction infusion port 902, and into the treatment site.

In an additional exemplary embodiment, system 900 may further comprise a data acquisition and processing system 908 operably coupled to sizing device 100 as shown in FIG. 9B, whereby data acquisition and processing system 908 is operable to receive conductance data from sizing device 100. In at least one embodiment, data acquisition and processing system 908 is further operable to calculate at least one luminal parameter based upon said conductance data. In at least another embodiment, data acquisition and processing system 908 is further operable to display the calculated at least one luminal parameter to facilitate operational control of treatment device 112. Said parameter, along with potentially other data and/or parameters, may be displayed on, for example, a display 910 operably coupled to data acquisition and processing system 908 as shown in FIG. 9B.

Figure 9C:
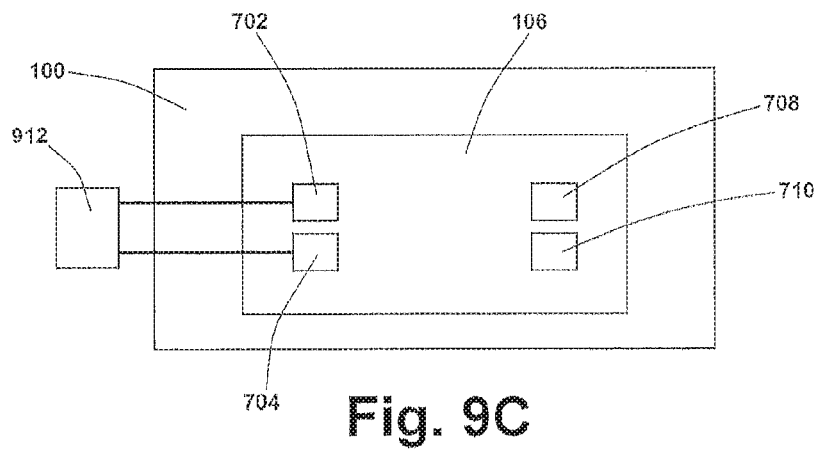
FIG. 9C shows an exemplary embodiment of a sizing device of the present disclosure.

In at least one embodiment of a system for removing a stenotic lesion of a vessel, and as shown in FIG. 9C, an exemplary sizing device 100 comprises at least one sizing portion 106. Sizing portion 106, as shown in the embodiment of sizing device 100 in FIG. 9C, may comprise a first excitation electrode 702, a second excitation electrode 704, a first detection electrode 708, and a second detection electrode 710, and may farther comprise a current source 912 in communication with first excitation electrode 702 and second excitation electrode 704. In at least one embodiment, current source 912 is operable to supply current to first excitation electrode 702 and second excitation electrode 704 to facilitate measurement of at least one conductance value, thereby facilitating calculation of a luminal size parameter.

In at least one method for removing a stenotic lesion of a vessel of the disclosure of the present application, the method comprises the steps of positioning a device within a vessel lumen, the device (for example, a combination device 400 as shown in FIGS. 4A-5C) comprising at least one sizing portion 106 and at least one treatment portion 114, and operating sizing portion 106 of combination device 400 to obtain luminal size parameter data. An exemplary method may further comprise the steps of operating treatment portion 114 at a location within the vessel lumen at or near a stenotic lesion 110, whereby operation of treatment portion 114 is based upon the luminal size parameter data, and whereby operation of treatment portion 114 increases the luminal size parameter data value. Such a method may further comprise the step of ceasing operation of treatment portion 114 of combination device 400 when the luminal size parameter data indicates a preferred luminal size parameter.

In at least one embodiment of a method for removing a stenotic lesion of a vessel of the disclosure of the present application, the luminal size parameter data is displayed on a display 910 (such as a computer monitor, other monitor, or LCD display, for example), and the step of operating treatment portion 114 is performed based upon the displayed luminal size parameter data. In an exemplary embodiment, the luminal size perimeter data comprises a first luminal size parameter obtained at a first location within the vessel lumen, a second luminal size parameter obtained at a second location within the vessel lumen, and at least one then-current luminal size parameter obtained after initial operation of the at least one treatment portion. Said parameters may be as previously described herein regarding one or more methods of the present disclosure, and may comprise, for example, diameters and/or cross-sectional areas. In at least one embodiment of such a method, the preferred luminal size parameter is determined based upon luminal size parameter data obtained at a location within the vessel lumen without a stenotic lesion 110. In another embodiment, the preferred luminal size parameter is larger than luminal size parameter data obtained at a location within the vessel lumen at or near a stenotic lesion.

In at least one embodiment of a sizing portion 106 of a combination device 400 operable to facilitate performance of one or more methods of the present disclosure, sizing portion 106 comprises a first excitation electrode 702 and a second excitation electrode 704 positioned along combination device 400 at or near a distal end 706 of combination device 400, and further comprises a first detection electrode 708 and a second detection electrode 710 positioned along combination device 400 in between first excitation electrode 702 and second excitation electrode 704. Such an embodiment may comprise an embodiment of a device similar to or the same as the embodiment of an exemplary sizing device 100 as shown in FIG. 7B. In addition, said combination device 400 may comprise one or more features, elements, and/or limitations of one or more other devices and/or systems (or portions thereof) referenced herein, including, but not limited to, an exemplary sizing device 100, an exemplary treatment device 112, and/or an exemplary system 900.

In addition to the foregoing, and in at least one embodiment of a method for removing a stenotic lesion of a vessel of the disclosure of the present application, the step of operating the at least one sizing portion 106 may comprise obtaining multiple luminal size parameter values during the step of operating the at least one treatment portion 114.

In at least one embodiment of a device for removing a stenotic lesion of a vessel of the disclosure of the present application, the device (for example, a combination device 400) comprises at least one sizing portion 106 and at least one treatment portion 114. Sizing portion 106 and/or treatment portion 114 may comprise one or more features, elements, and/or limitations of one or more other devices and/or systems (or portions thereof) referenced herein, including, but not limited to, an exemplary sizing device 100, an exemplary treatment device 112, and/or an exemplary system 900.

Figure 10A:
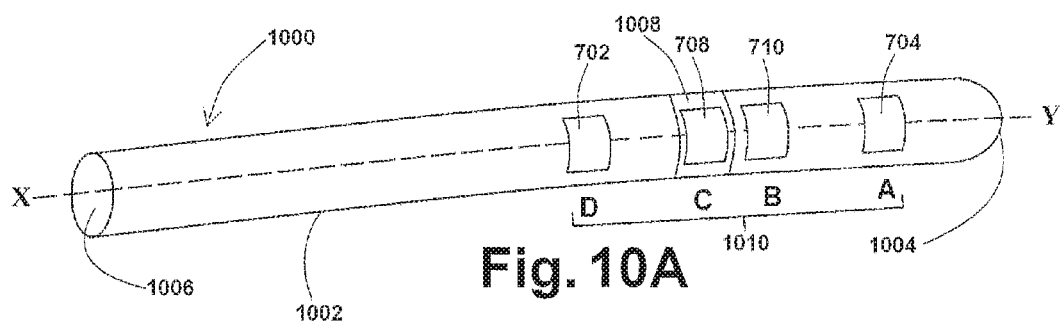
FIG. 10A shows an exemplary sizing/typing device of the present disclosure.
Figure 10B:
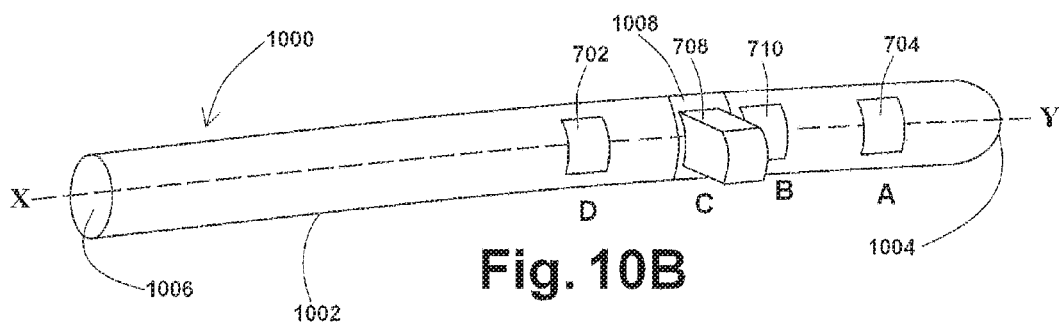
FIG. 10B shows an exemplary sizing/typing device of the present disclosure with an electrode extended therefrom, according to an embodiment of the present disclosure.
Figure 10C:
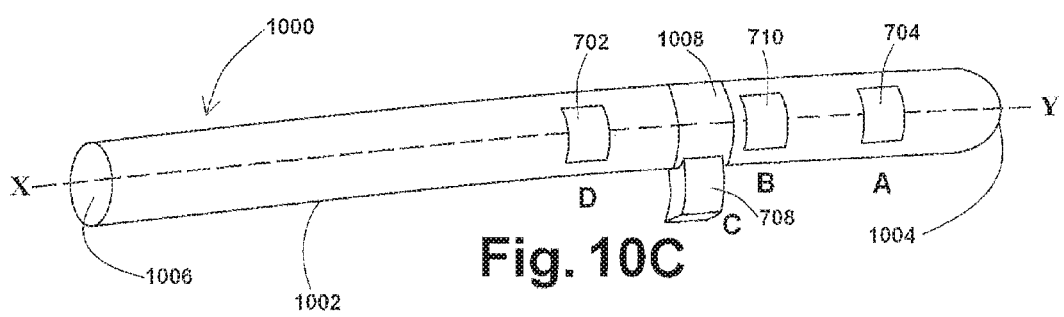
FIG. 10C shows an exemplary sizing/typing device of the present disclosure with an electrode extended therefrom and rotated, according to an embodiment of the present disclosure.

Various additional embodiments of devices of the present disclosure are shown in FIGS. 10A-10C. In at least one embodiment of at least a portion of a sizing/typing device 1000 of the present disclosure, and as shown in FIG. 10A, sizing/typing device 1000 comprises an elongated body 1002 having a longitudinal axis extending from a proximal end to a distal end 1004 (as indicated by the dotted line extending from "X" to "Y" as shown in FIG. 10A), whereby said sizing/typing device 1000 is configured to fit within a lumen of a luminal organ. An exemplary sizing/typing device 1000 of the present disclosure comprises a first excitation electrode 702 and a second excitation electrode 704 positioned along the longitudinal axis of the elongated body 1002 at or near a distal end 1004 of the elongated body 1002, and further comprises a first detection electrode 708 and a second detection electrode 710 positioned along the longitudinal axis of the elongated body 1002 in between the first excitation electrode 702 and the second excitation electrode 704. As shown in FIG. 10A, second excitation electrode 704 may be referred to as electrode "A", second detection electrode 710 may be referred to as electrode "B", first detection electrode 708 may be referred to as electrode "C", and first excitation electrode 702 may be referred to as electrode "D", and are shown in an exemplary tetrapolar arrangement. In at least one exemplary embodiment of a sizing/typing device 1000, and as shown in FIGS. 10A and 10B, the elongated body 1002 comprises a catheter having a lumen 1006 extending along the longitudinal axis of the catheter.

The exemplary embodiment of at least a portion of a sizing/typing device 1000 shown in FIG. 10A, as well as various other embodiments of sizing/typing devices 1000 of the present disclosure, comprise "directional electrodes" or "directional sensors," meaning that they do not completely extend the entire circumference of sizing/typing devices 1000. As shown in FIG. 10A, an exemplary embodiment of a sizing/typing device 1000 of the present disclosure comprises directional electrodes (702, 708, 710, and 704, for example, which may be referred to generally herein as an exemplary detector 1010) positioned along elongated body 1002 at approximately 90° around a 360° circumference of sizing/typing device 1000. In at least another embodiment, said electrodes (and directional sensors 1200 as referenced below) are positioned at approximately 45° around a 360° circumference of sizing/typing device 1000. These directional electrodes, as discussed in further detail herein, allow a user of said sizing/typing device 1000 to obtain impedance measurements, for example, at a portion of a vessel instead of obtaining impedance measurements indicative of an entire circumference of a vessel at the location of said electrodes. Such measurements, and other measurements obtainable from exemplary detectors 1010 of the present disclosure, may be generally referred to as various "luminal size parameters" indicative of, for example, luminal cross-sectional areas or luminal diameters. In addition, such directional measurements overcome the problems associated with average measurements at one location within a vessel, and may identify when a vessel is not circumferentially uniform, as parts of a vessel at a single location may be calcified, fibrotic, contain lipids, or be "normal."

Figure 20:
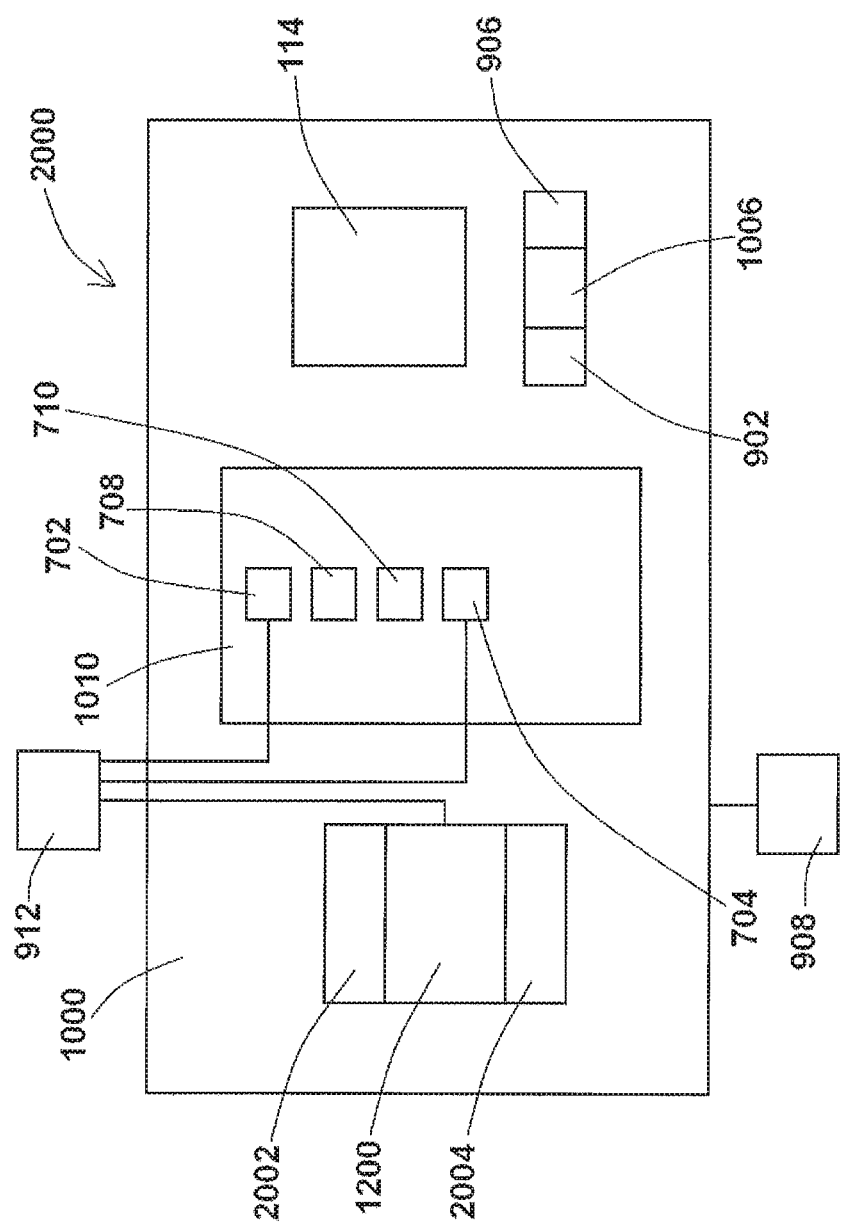
FIG. 20 shows an exemplary embodiment of a system useful for removing stenotic lesions from vessels, according to the present disclosure.

As shown in FIG. 10A, an exemplary sizing/typing device 1000 of the present disclosure comprises at least one rotatable portion 1008. Rotatable portion 1008 allows at least one electrode of sizing/typing device 1000 to rotate around a circumference of sizing typing device 1000, allowing a user to obtain directional impedance measurements, for example, at various portions of a vessel wall. Rotation may be facilitated by a rotation apparatus 2002 (as shown in FIG. 20), which may be a mechanical actuator, an electro-mechanical actuator, and/or a steering device. Rotation apparatus 2002, in at least one embodiment, is capable of rotating rotatable portion 1008 a full 360° around elongated body 1002 (or wire 1300 as referenced below).

In an exemplary sizing/typing device 1000 of the present disclosure, at least one of electrodes A, B, C, and D is capable of extending outward from sizing/typing device 1000. For example, and as shown in FIG. 10B, electrode C (first detection electrode 708) is not only positioned within rotatable portion 1008, but also is capable of extending outward from sizing/typing device 1000. Such an extension, for example, allows electrode C (or another electrode/sensor of the present disclosure that is capable of extending outward from a first position to an extended second position) to physically touch a vessel wall and/or a substance present within or on a vessel wall, such as a stenotic lesion or a lipid mass. Extension of C (or another electrode/sensor of the present disclosure, such as a directional sensor 1200 referenced herein) may be facilitated by an extension apparatus 2004 (as shown in FIG. 20), which may also be a mechanical actuator, an electro-mechanical actuator, and/or a steering device.

This physical touching, as described in further detail below, provides a user of a sizing/typing device 1000 with the ability to determine what such an electrode is touching (vessel wall, lesion, etc.), so that a determination can be made as to whether or not to perform any treatment within the vessel at that particular location. For example, if an electrode/sensor of sizing/typing device 1000 extends therefrom and physically touches a vessel wall without a lesion, a user of sizing/typing device 1000 may decide not to, for example, operate a treatment device or a treatment portion of sizing/typing device 1000 at that particular location so not to damage the vessel wall. Alternatively, if an electrode/sensor of sizing/typing device 1000 extends therefrom and physically touches a stenotic lesion within a vessel wall, a user of sizing/typing device 1000 may decide to operate a treatment device or a treatment portion of sizing/typing device 1000 at that particular location to remove at least part of the lesion.

FIG. 10C shows an exemplary embodiment of at least a portion of a sizing/typing device 1000 of the present disclosure, whereby rotatable portion 1008 has rotated from its original position shown in FIG. 10B. In at least one embodiment, rotatable portion 1008 is capable of a full 360° rotation about sizing/typing device 1000.

Figure 11A:
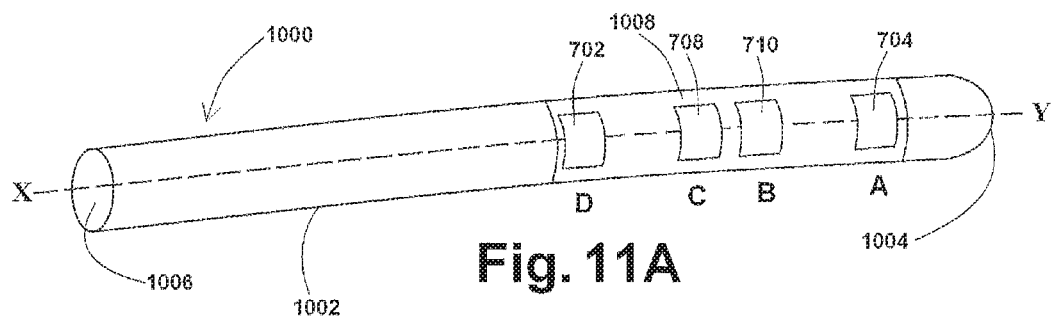
FIGS. 11A-11C show various embodiments of sizing/typing devices according to the present disclosure.
Figure 11B:
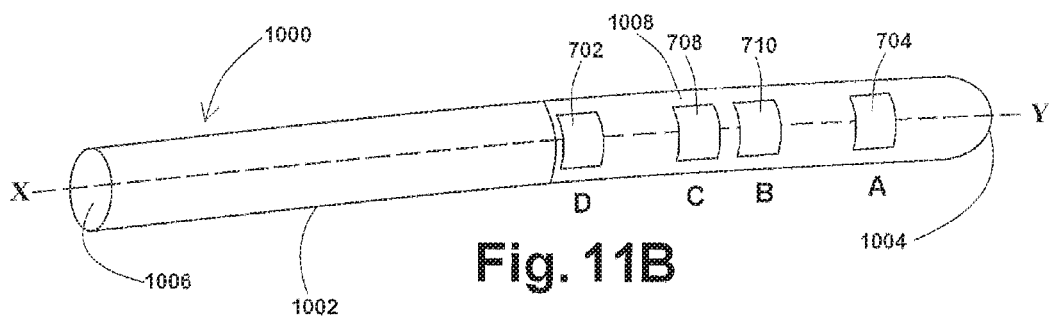
Figure 11C:
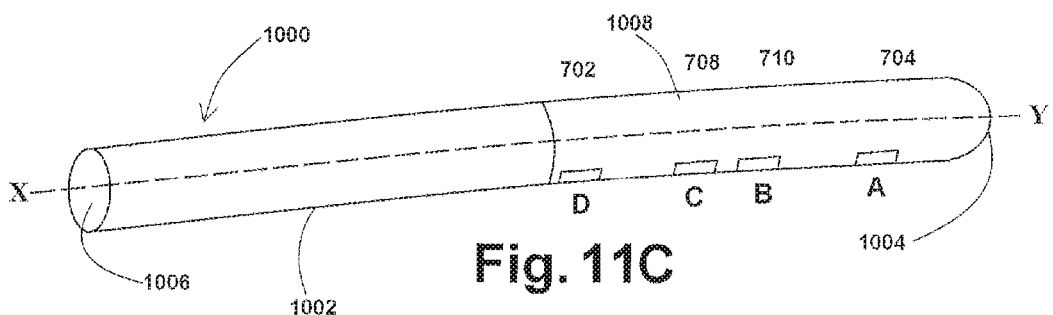

Additional embodiments of sizing/typing devices 1000 of the present disclosure are shown in FIGS. 11A-11C. In at least one embodiment of at least a portion of a sizing/typing device 1000 of the present disclosure, and as shown in FIG. 11A, sizing/typing device 1000 comprises an elongated body 1002 having a longitudinal axis extending from a proximal end to a distal end 1004 (as indicated by the dotted line extending from "X" to "Y" as shown in FIG. 10A), and electrodes A, B, C, and D as referenced above. In at least the embodiment shown in FIG. 11A, sizing/typing device 1000 comprises a rotatable portion 1008 whereby each of electrodes A, C, and D are present thereon. In at least another embodiment, and as shown in FIGS. 11B and 11C, sizing/typing device 1000 comprises a rotatable portion 1008 whereby the entire distal portion of sizing/typing device 1000 may rotate, noting that in the embodiment shown in FIG. 11A, the most distal end is not part of rotatable portion 1008. FIG. 11B shows an exemplary sizing/typing device 1000 with a rotatable portion 1008 in a first position, and FIG. 11C shows an exemplary sizing/typing device 1000 with a rotatable portion 1008 in a second position rotated from the first position.

In a situation where a user of a sizing/typing device 1000 of the present disclosure desires to have the least amount of rotatable matter, a sizing/typing device 1000 as shown in FIGS. 10A-10C may be preferred. If the amount of rotatable matter is not of particular concern, any number of embodiments of sizing/typing devices 1000 of the present disclosure may be useful depending on the particular application.

Figure 12A:
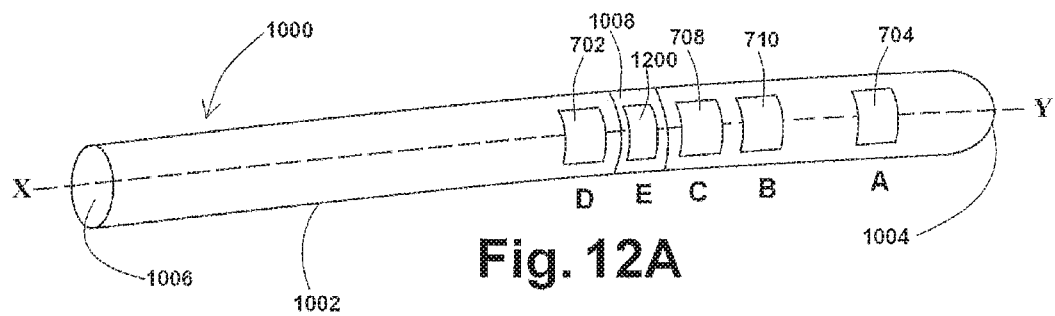
FIGS. 12A-12C show various embodiments of sizing/typing devices having directional sensors thereon, according to the present disclosure.
Figure 12B:
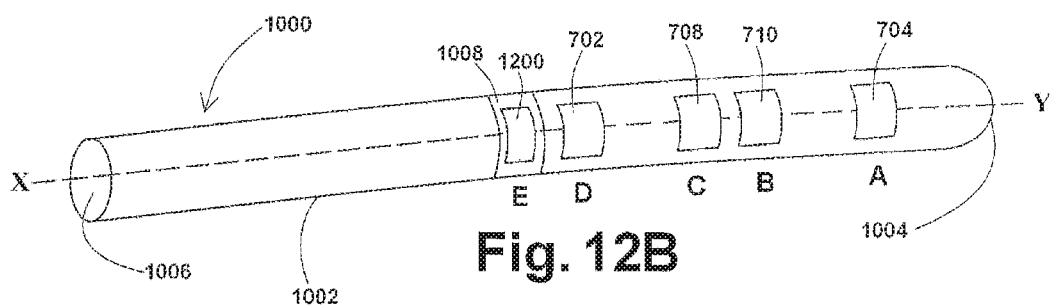
Figure 12C:
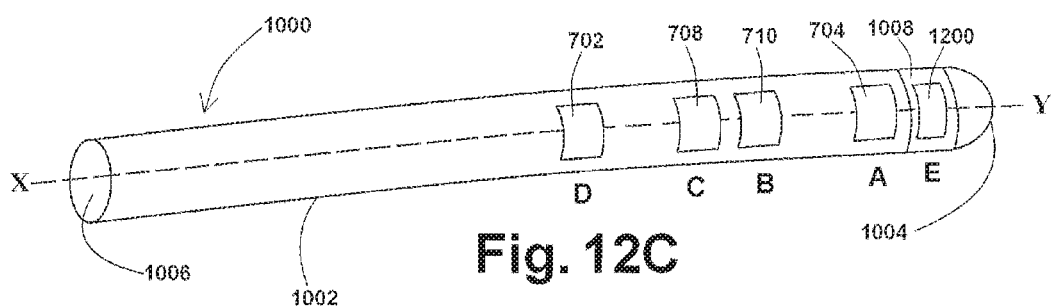

At least another embodiment of a sizing/typing device 1000 of the present disclosure is shown in FIG. 12A. As shown in FIG. 12A, sizing/typing device 1000 comprises an elongated body 1002 having a longitudinal axis extending from a proximal end to a distal end 1004 (as indicated by the dotted line extending from "X" to "Y" as shown in FIG. 10A), and further comprises electrodes A, B, C, and D as referenced herein. However, in at least the exemplary embodiment shown in FIG. 12A, sizing/typing device 1000 comprises a directional sensor 1200, whereby directional sensor 1200 appears along elongated body 1002 within a rotatable portion 1008 of elongated body 1002. In at least one embodiment, directional sensor 1200 is capable of extending outward from elongated body 1000 (similar to electrode C as shown in FIG. 10B), and is further capable of rotation about elongated body 1002 (similar to electrode C as shown in FIG. 10C). In addition, and as shown in FIGS. 12B and 12C, directional sensor 1200 may be positioned at various places along sizing/typing device 1000, such as, for example, proximal to electrodes A, B, C, and D (as shown in FIG. 12B), or distal to electrodes A, B, C, and D (as shown in FIG. 12C). In each embodiment, for example, directional sensor 1200 may be positioned along elongated body 1002 at a rotatable portion 1008 so that directional sensor 1200 may rotate as referenced herein. Furthermore, more than one directional sensor 1200 may be used in various embodiments of sizing/typing devices 1000 of the present disclosure.

In various embodiments of sizing/typing devices 1000 of the present disclosure, directional sensor 1200 is capable of extending outward to physically touch a luminal organ or a structure therein when an exemplary sizing/typing device 1000 is positioned within a lumen of a luminal organ. In additional embodiments, directional sensor 1200 is capable of obtaining a measurement from the luminal organ or the structure therein that is indicative of what directional sensor 1200 is touching. For example, if directional sensor 1200 comprises an impedance sensor, then the measurement is an impedance measurement which is indicative of what directional sensor 1200 is touching. If a constant voltage is applied to directional sensor 1200, the measurement is a current measurement, and similarly, if a constant current is applied to directional sensor 1200, the measurement is a voltage measurement. In an embodiment where directional sensor 1200 comprises a thermistor, for example, the measurement is a temperature measurement, which itself is indicative of what directional sensor 1200 is touching within the luminal organ.

Figure 13A:
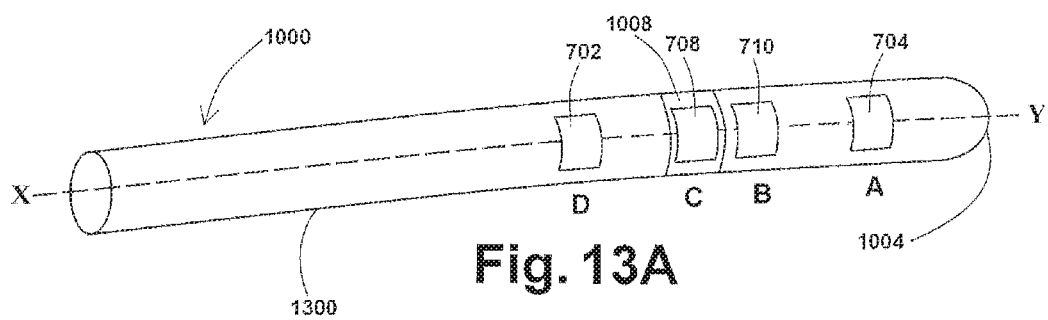
FIGS. 13A-14C show various embodiments of wire forms of sizing/typing devices according to the present disclosure.
Figure 13B:
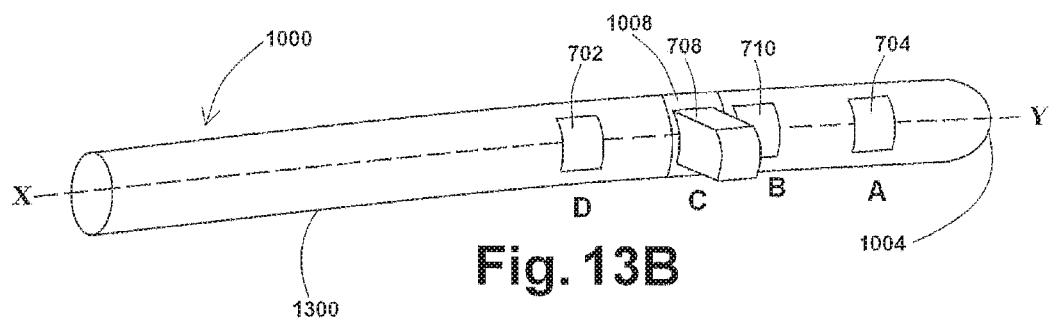
Figure 13C:
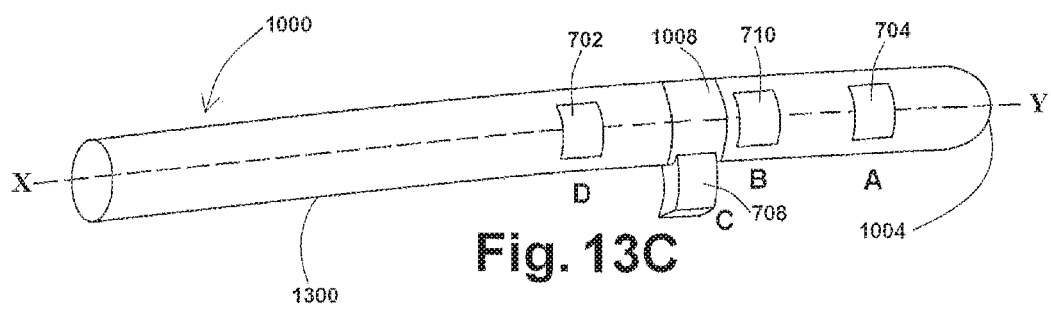

Various additional embodiments of sizing/typing devices 1000 of the present disclosure are shown in FIGS. 13A-13C. As shown in FIGS. 13A-13C, sizing/typing device 1000 comprises a wire 1300, whereby electrodes A, B, C, and D are positioned directionally thereon at or near a distal end 1004 of wire 1300. In the exemplary embodiments shown therein, electrode C may rotate about wire 1300 (at rotatable portion 1008) as shown in FIG. 13C, and may extend outwardly from wire 1300 as shown in FIG. 13B. In such exemplary embodiments and other potential embodiments, electrodes A, B, C, and D may themselves comprise wire electrodes with electrode/sensor tips.

Figure 14A:
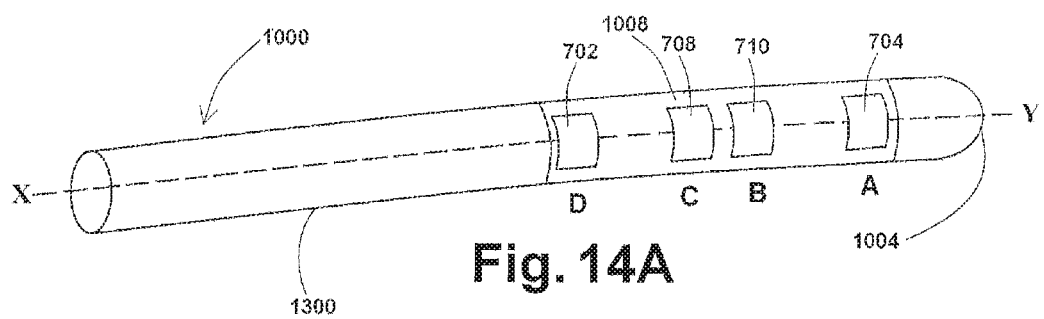
Figure 14B:
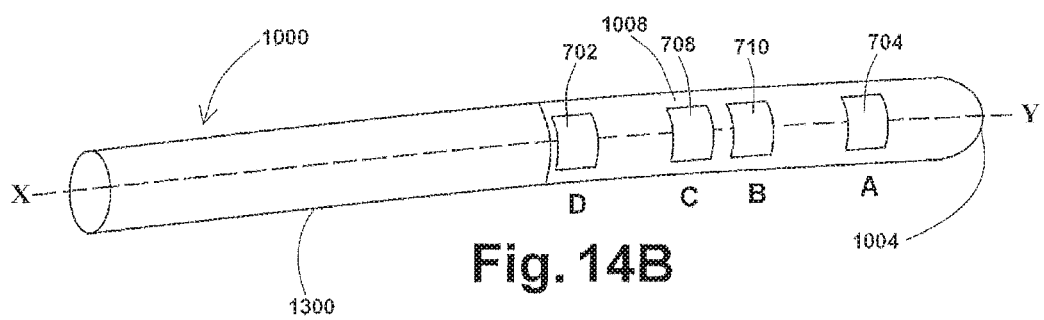
Figure 14C:
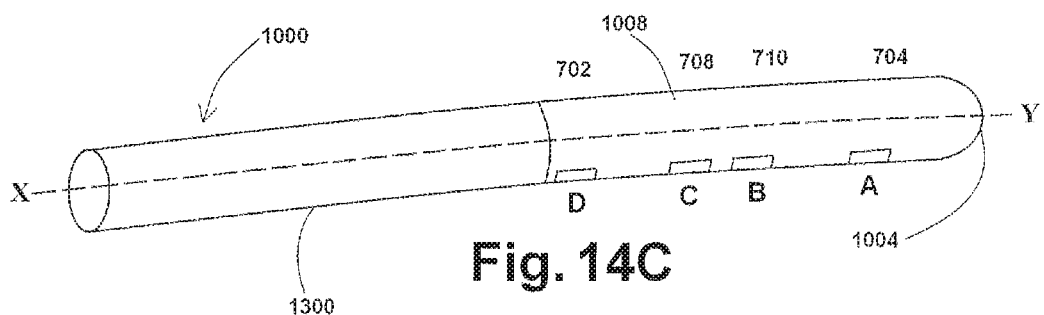

Additional embodiments of sizing/typing devices 1000 of the present disclosure are shown in FIGS. 14A-14C. As shown in FIGS. 14A-14C, sizing/typing devices 1000 comprise wires 1300, whereby rotatable portions 1008 shown therein include each of electrodes A, B, C, and D, and/or the tip of sizing devices 1000 near their respective distal ends.

Figure 15A:
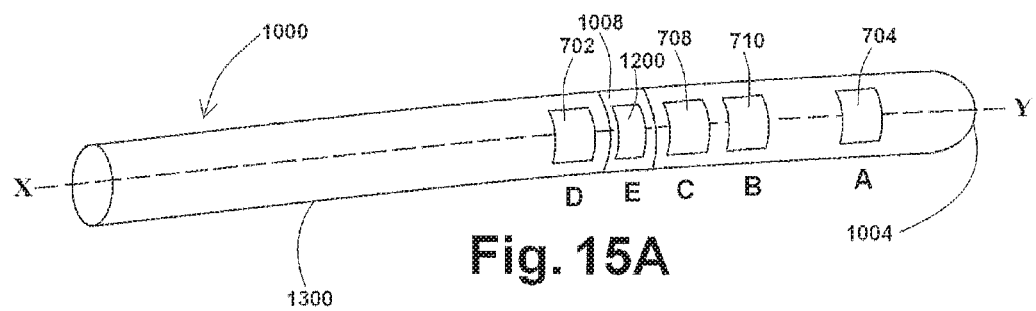
FIGS. 15A-15C show various embodiments of wire forms of sizing/typing devices having directional sensors thereon, according to the present disclosure.
Figure 15B:
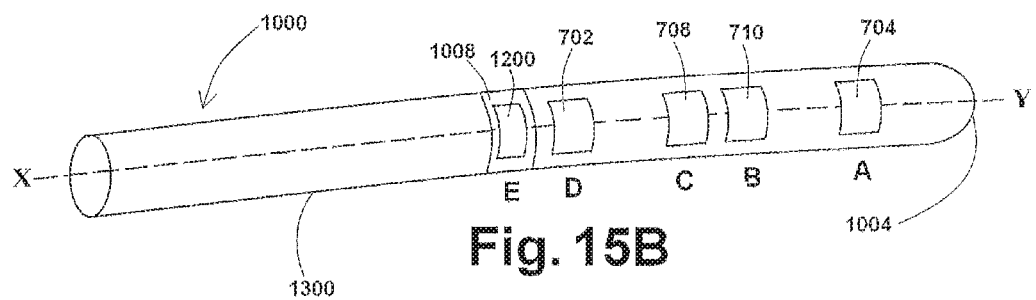
Figure 15C:
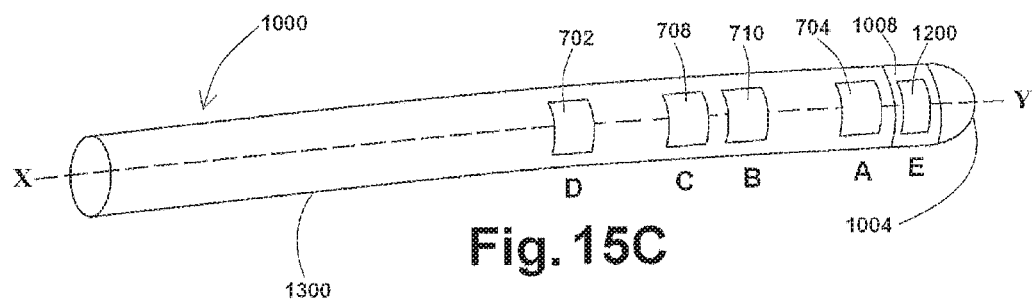

FIGS. 15A-15C show additional embodiments of sizing/typing devices 1000 of the present disclosure. As shown in FIGS. 15A-15C, sizing/typing devices 1000 comprise a directional sensor 1200 within a rotatable portion 1008 of sizing/typing devices 1000 in addition to electrodes A, B, C, and D, whereby directional sensor 1200 is positioned along wire 1300 within electrodes A, B, C, and D) (FIG. 15A), proximal to said electrodes (FIG. 15B), and distal to said electrodes (FIG. 15C).

Figure 16A:
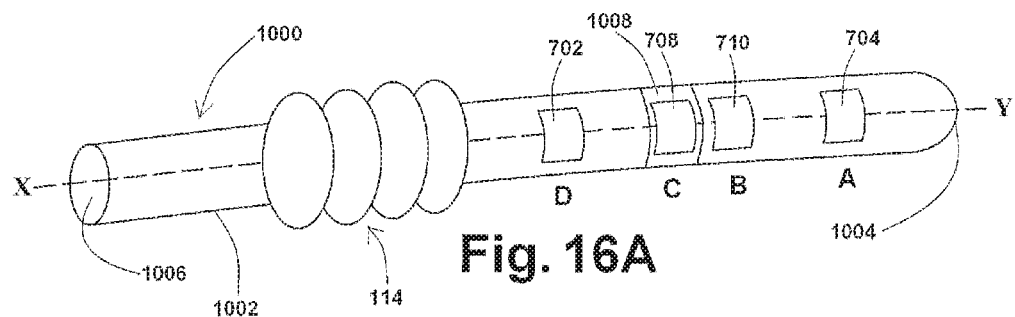
FIGS. 16A-16C show various embodiments of sizing/typing devices comprising treatment portions, according to the present disclosure.
Figure 16B:
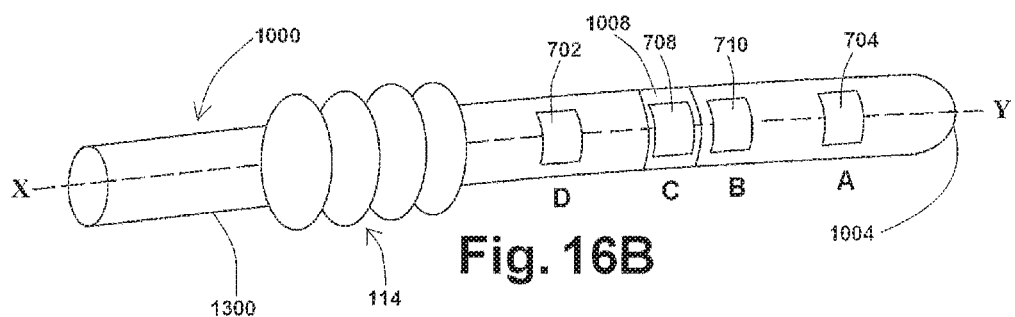
Figure 16C:
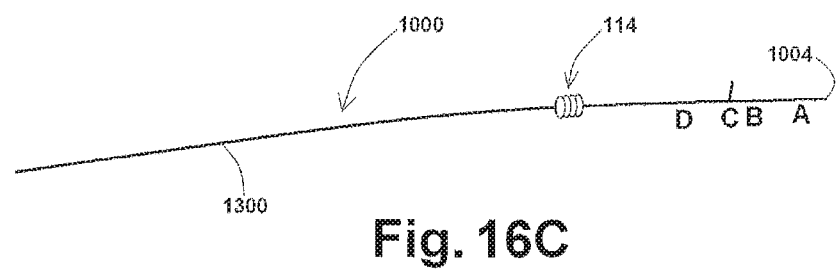

Exemplary embodiments of sizing/typing devices 1000 of the present disclosure having one or more treatment portions positioned thereon are shown in FIGS. 16A-16C. As shown in FIG. 16A, sizing/typing device 1000 comprises an elongated body 1002 having a lumen therethrough, whereby a treatment portion 114 is positioned thereon proximal to electrodes A, B, C, and D. FIG. 16B shows an exemplary sizing/typing device 1000 comprising a wire 1300 and a treatment portion 114 is positioned thereon proximal to electrodes A, B, C, and D. Treatment portions 114 of sizing/typing devices 1000 may comprise any number of treatment portions 114 referenced herein or known in the art including, but not limited to, a cutting balloon, a cryoplasty device, a rotational atherectomy device, a laser angioplasty device, a vibrating catheter, a vibrating blade, and a vibrating drill.

An additional exemplary embodiment of a sizing/typing device 1000 of the present disclosure having a treatment portion 114 thereon is shown in FIG. 16C. As shown in FIG. 16C, sizing/typing device 1000 comprises a wire 1300 having electrodes A, B, C, and D at or near a distal end 1004 of sizing/typing device 1000. In this exemplary embodiment, electrode C is capable of rotation and extension as referenced herein, whereby the rotation of electrode C allows directional impedance measurements to be obtained, and whereby the extension of electrode C from wire 1300 allows electrode C to physically touch a vessel wall or a body within a vessel wall (such as a plaque, for example), to allow a determination of the type of tissue/structure said electrode is touching. The exemplary embodiment shown in FIG. 16C comprises a treatment portion 114, so that such an embodiment of a sizing/typing device 1000 can perform three separate tasks, including sizing of a vessel, typing a vessel or vessel structure, and treatment of a vessel to, for example, remove a stenotic lesion.

Figure 17A:
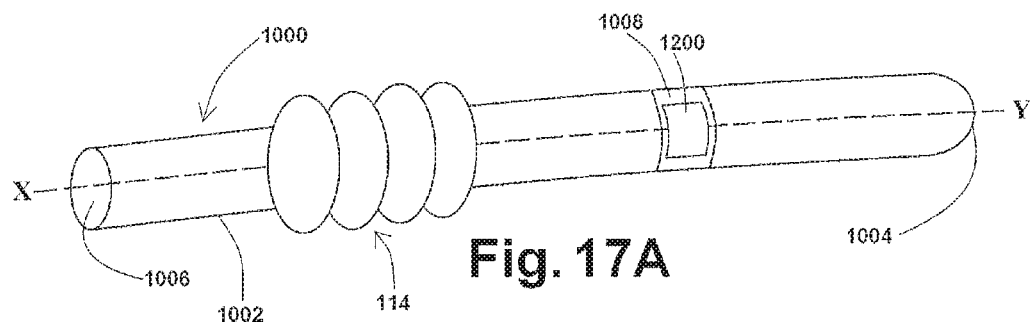
FIGS. 17A-17C show various embodiments of sizing/typing devices having directional sensors and treatment portions thereon, according to the present disclosure.
Figure 17B:
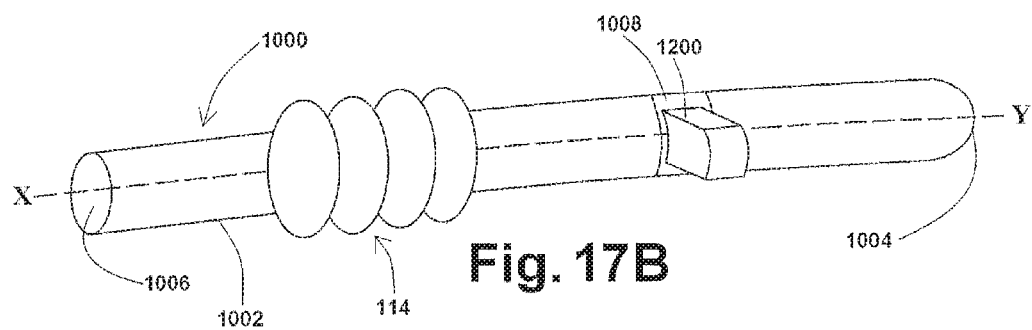
Figure 17C:
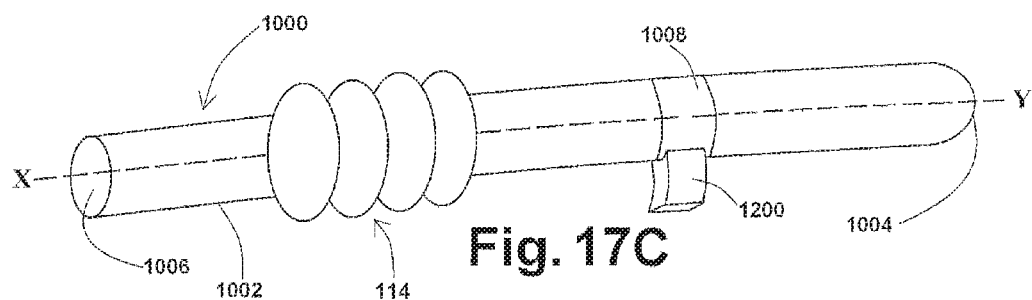
Figure 18A:
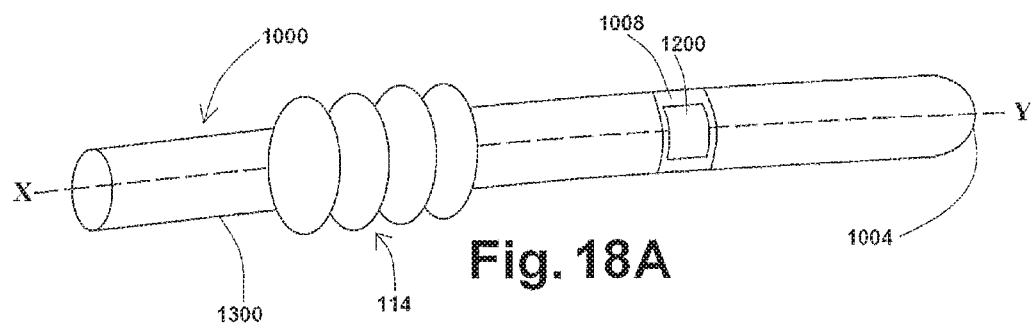
FIGS. 18A-18C show various embodiments of wire forms of sizing/typing devices having directional sensors and treatment portions thereon, according to the present disclosure.
Figure 18B:
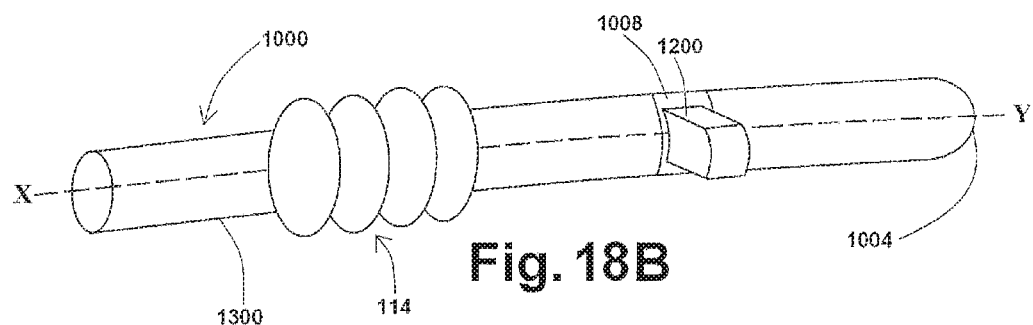
Figure 18C:
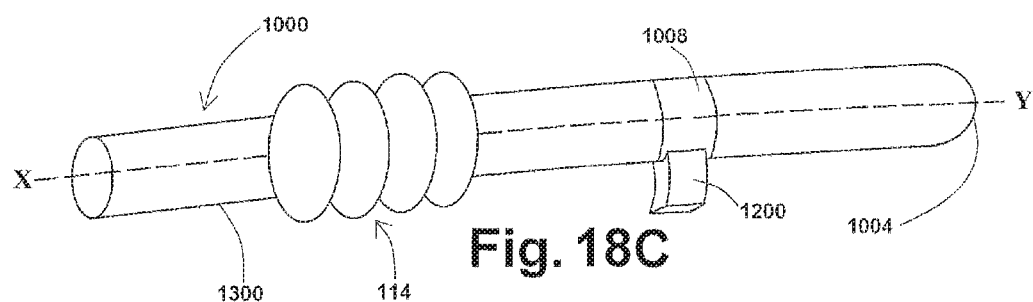

Additional exemplary embodiments of sizing/typing devices 1000 of the present disclosure are shown in FIGS. 17A-18C. As shown in FIGS. 17A-17C, sizing/typing devices 1000 comprise an elongated body 1002, and directional sensor 1200 within a rotatable portion 1008 of elongated body 1002, and a treatment portion 114. FIG. 17A shows an embodiment of sizing/typing device 1000 with directional sensor 1200 at a first position, FIG. 17B shows directional sensor 1200 in an extended position, and FIG. 17C shows directional sensor 1200 in an extended position and rotated from its original position along elongated body 1002. FIGS. 18A-18C show exemplary sizing/typing devices 1000 of the present disclosure comprising a directional sensor 1200 within a rotatable portion 1008 of a wire 1300, and further comprising an exemplary treatment portion 114 of the present disclosure. FIGS. 18A, 18B, and 18C show directional sensor in an initial position, extended, and rotated, respectively.

Figure 19A:
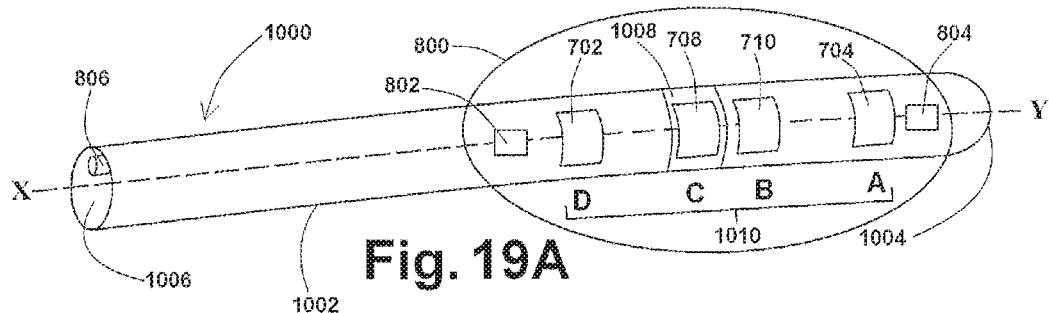
FIG. 19A shows an exemplary embodiment of a sizing/typing device comprising a balloon coupled thereto, according to an embodiment of the present disclosure.

In an exemplary embodiment of a sizing/typing device 1000 of the present disclosure wherein an exemplary treatment portion 114 comprises a balloon 800 (as shown, for example, in FIG. 19A, discussed below), electrodes A, B, C, and D may each be positioned along sizing/typing device 1000 within balloon 800, and wherein a then-current luminal size parameter (obtained by electrodes A, B, C, and D) comprises a parameter measured within balloon 800 at one or more stages of balloon 800 inflation. As shown in FIG. 19A, an exemplary sizing/typing device 1000 comprises balloon 800 surrounding the various electrodes positioned along the elongated body 1002 (or wire 1300 in a wire embodiment) of sizing/typing device 1000. In an exemplary embodiment, pressure sensor 802 is capable of detecting at least one pressure within balloon 800 at one or more stages of balloon 800 inflation. As shown in FIG. 19A, balloon 800 may inflate and/or deflate via inflation/deflation port 804, allowing a gas and/or a liquid to be introduced into or removed from balloon 800 via suction/infusion tube 806.

Figure 19B:
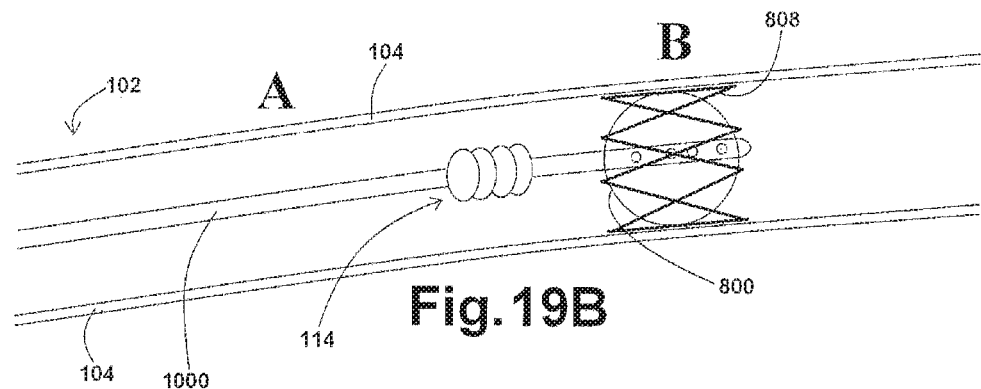
FIGS. 19B and 19C show exemplary embodiments of sizing/typing devices placing stents within a vessel, according to the present disclosure.
Figure 19C:
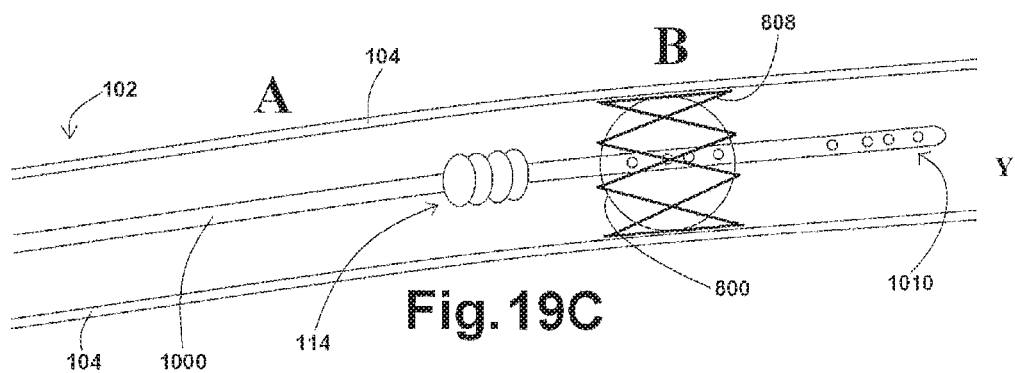

As shown in FIG. 19B, an exemplary sizing/typing device 1000 of the present application comprises a balloon 800 coupled thereto, and is shown in an inflated state while positioning a stent 808 within the lumen of a vessel 102. In another embodiment, and as shown in FIG. 19C, sizing/typing device 1000 is shown performing a similar procedure, noting that in this exemplary embodiment, sizing/typing device 1000 comprises a treatment portion 114, a detector 1010, and a balloon 800 positioned around various electrodes (such as a set of electrodes A, B, C, and D).

An exemplary embodiment of a system of the present disclosure is shown in FIG. 20. As shown in FIG. 20, system 2000 comprises a sizing/typing device 1000 comprising a directional sensor 1200 coupled to a rotation apparatus 2002 and an extension apparatus 2004. Detector 1010 comprises electrodes first excitation electrode 702, second excitation electrode 704, first detection electrode 708, and second detection electrode 710, whereby a current/voltage source 902 is coupled to directional sensor 1200, first excitation electrode 702, and second excitation electrode 704. Sizing/typing device 1000 may further define a lumen 1006, whereby a suction/infusion port 902 is defined at or near one end of sizing/typing device 1000, and a fluid delivery source may be coupled to sizing device 1000 at another end of said device 1000. Sizing/typing device 1000 of system 2000 may further comprise at least one treatment portion 114, and may be coupled to a data acquisition and processing system 908. Each of the aforementioned components of device 1000 and/or system 2000 may function/operate as described in the present disclosure.

Figure 21:
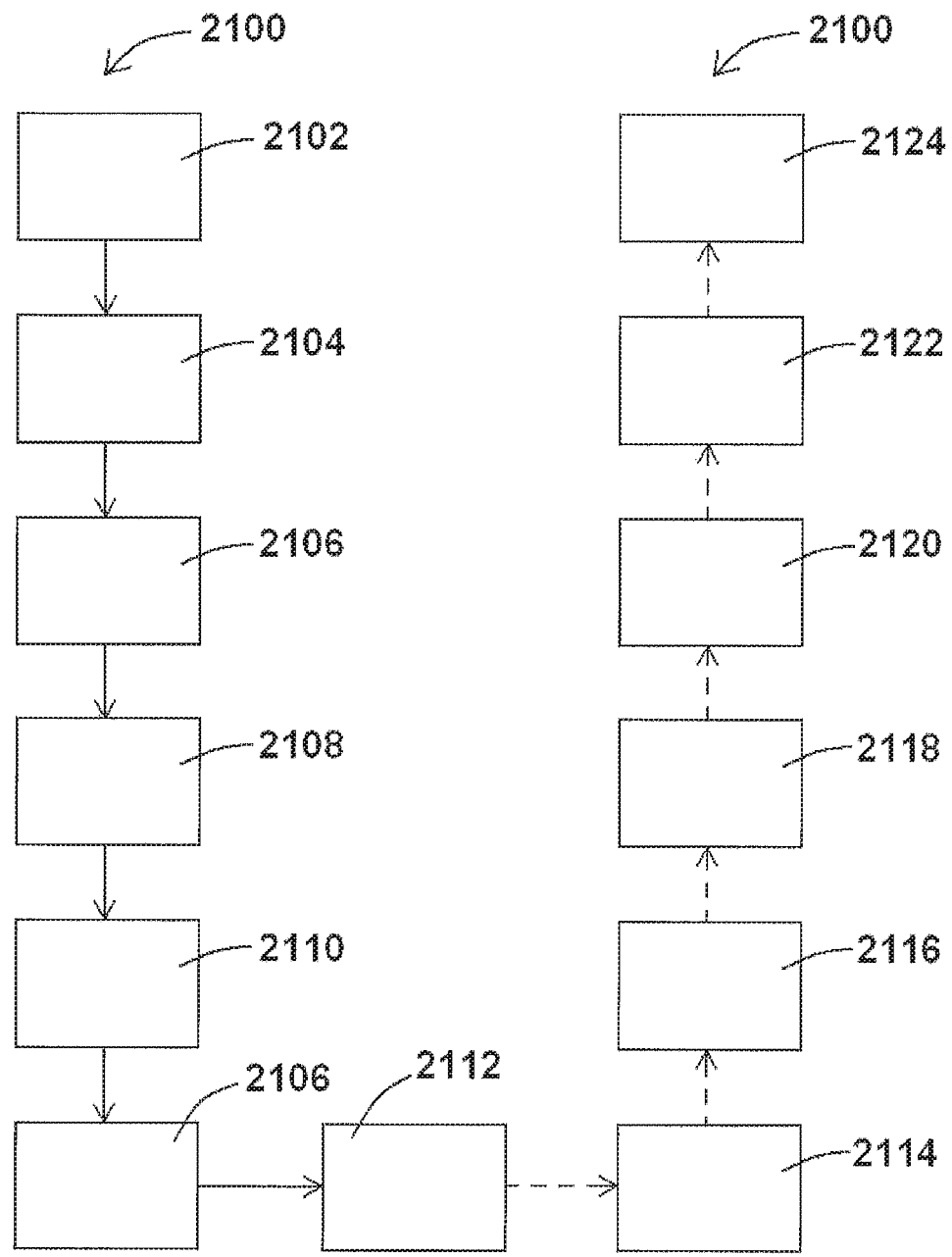
FIGS. 21, 22A, and 22B show steps of exemplary methods of using a sizing/typing device of the present disclosure.

Steps of using an exemplary sizing/typing device 1000 of the present disclosure are shown in FIG. 21. As shown in FIG. 21, an exemplary method 2100 of using a sizing/typing device 1000 of the present disclosure comprises the steps of positioning at least part of a sizing/typing device 1000 within a luminal organ at a first location (an exemplary positioning step 2102) and operating sizing/typing device 1000 to obtain a first luminal size parameter and a first measurement indicative of electrical impedance of the luminal organ or a structure therein that at least part of sizing/typing device 1000 is physically touching at the first location (an exemplary first operation step 2104). Step 2104 may be performed in the presence of a saline injection to optimize the output readings as referenced herein.

The first measurement indicative of electrical impedance of the luminal organ or a structure therein allows a user of sizing/typing device 1000 to know what, for example, directional sensor 1200 is touching. For example, and in an embodiment where a constant current is applied to directional sensor 1200 when directional sensor 1200 is touching the luminal organ or a structure therein (such as a plaque), a voltage can be measured and a resulting impedance can be determined based on Ohm's law (V=I/R, where V=voltage, I=current, and R=resistance or impedance in the case of alternating current). If instead a constant voltage is applied, a current can be measured and a resulting impedance can be determined. Physically, lipid and calcium (calcifications, such as stenotic lesions) have notably different impedance characteristics than a normal vessel wall. An exemplary study has shown that, for example, the electrical conductivities at 30 Hz for muscle, blood vessels, fat, and bone marrow (similar to a hard plaque) are 0.350, 0.32, 0.024, and 0.003 S/m. Similarly, a stenotic lesion and a normal vessel have different temperature characteristics, and in an embodiment of a sizing/typing device 1000 of the present disclosure wherein a directional sensor comprises a thermistor (temperature sensor), physically touching a vessel or a substance therein, especially in the presence of a saline injection to optimize the results, would provide temperature data indicative of what directional sensor 1200 is physically touching. Therefore, by knowing the impedance, a user of sizing/typing device knows what directional sensor 1200 is touching at that time, which may be, for example, calcifications, lipids, fibrosis, normal tissue, plaque components, and the like. Such measurements (as well as measurements in connection with vessel sizing as referenced herein) can be made in the presence of a saline injection, for example, to standardize the impedance measurements by eliminating the variability of the conductance of blood since saline has a known conductivity. The saline injections may also be advantageous for temperature measurements (as generally referenced herein) with a thermistor to detect thermal maps in the presence of reduced viscous drag forces as compared to blood, which has a higher viscosity.

Method 2100 may further comprise the steps of moving at least part of sizing/typing device 1000 to a second location within the luminal organ (an exemplary moving step 2106), operating sizing/typing device 1000 to obtain a second luminal size parameter and a second measurement indicative of electrical impedance of the luminal organ or the structure therein that at least part of the device is physically touching at the second location (an exemplary second operation step 2108) and determining whether or not a stenotic lesion is present at either the first location or the second location based on one or more of the first luminal size parameter, the first measurement, the second luminal size parameter, and the second measurement (an exemplary determination step 2110). If a stenotic lesion is present, method 2100 may further comprise the steps of moving at least part of sizing/typing device 1000 having a treatment portion 114 to a stenotic lesion location (another exemplary moving step 2106), and operating treatment portion 114 of sizing/typing device 1000 to remove at least part of the stenotic lesion (an exemplary treatment step 2112).

In at least one embodiment of a method 2100 of the present disclosure, and as shown in FIG. 21, method 2100 comprises the steps of measuring a then-current luminal size parameter at the stenotic lesion location (an exemplary measurement step 2114), comparing the then-current luminal size parameter to either the first luminal size parameter or the second luminal size parameter that is indicative of the stenotic lesion location (an exemplary comparison step 2116), and if the then-current luminal size parameter does not equal a preferred luminal size parameter, repeating steps 2112, 2114, and 2116 until the then-current luminal size parameter equals or exceeds the preferred luminal size parameter (an exemplary repeat step 2118). In an exemplary embodiment of method 2100, the preferred luminal size parameter is determined based upon the first luminal size parameter and the second luminal size parameter.

In various embodiments of methods 2100 of the present disclosure, the step of moving at least part of the device to a second location (the first exemplary moving step 2106 referenced above) comprises advancing or retracting at least part of sizing/typing device 1000 within the luminal organ and/or comprises rotating at least part of sizing/typing device 1000 within the luminal organ. In at least one embodiment, the first luminal size parameter, the second luminal size parameter, and then-current luminal parameter(s) are obtained using a detector 1010 coupled to sizing/typing device 1000. In an exemplary embodiment, the first measurement and the second measurement are obtained using a directional sensor 1200 coupled to sizing/typing device 1000.

In at least one embodiment of a method 2100 of the present disclosure, exemplary measurement step 2114 further comprises measuring a then-current measurement indicative of electrical impedance of the luminal organ or structure therein, and comparison step 2116 further comprises comparing either the first measurement or the second measurement to the then-current measurement. In an exemplary embodiment, steps 2112, 2114, and 2116 are repeated if the then-current luminal size parameter does not equal a preferred luminal size parameter or if the then-current measurement is indicative of the stenotic lesion.

In various embodiments of methods 2100 of the present disclosure as shown in FIG. 21, method 2100 further comprises the step of ceasing the operation of treatment portion 114 of sizing/typing device 1000 when the then-current luminal size parameter equals or exceeds the preferred luminal size parameter (an exemplary treatment cessation step 2120). In additional embodiments, method 2100 further comprises the steps of selecting an appropriately-sized stent (an exemplary stent selection step 2122), and implanting the stent into the luminal organ (an exemplary stent implantation step 2124).

Figure 22A:
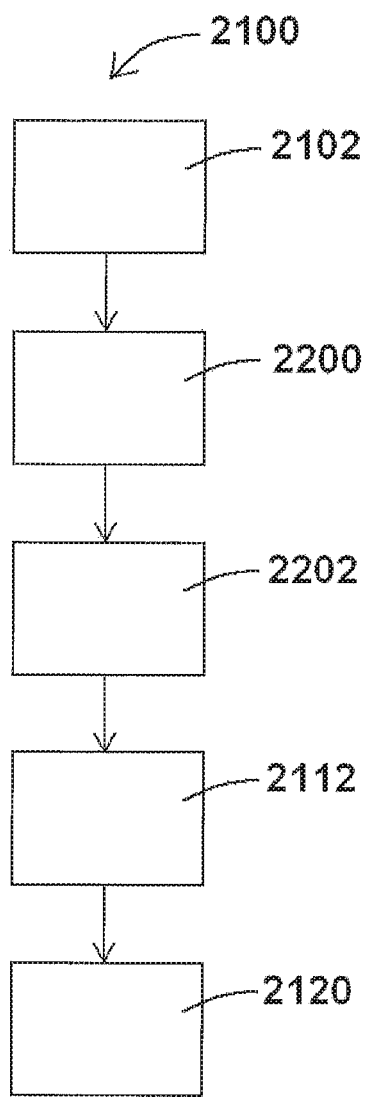

In at least one exemplary method 2100 of the present disclosure, and as shown in FIG. 22A, method 2100 comprises the steps of positioning a device within a luminal organ, the device comprising at least one sizing portion, at least one typing portion, and at least one treatment portion (another exemplary positioning step 2102), operating the at least one sizing portion of the device to obtain luminal size parameter data (an exemplary sizing step 2200), and operating the at least one typing portion of the device to obtain type data indicative of the luminal organ or a structure therein (an exemplary typing step 2202). Method 2100 may further comprise the step of operating the at least one treatment portion at a location within the luminal organ at or near a stenotic lesion, whereby operation of the at least one treatment portion is based upon the luminal size parameter data and the type data, whereby operation of the at least one treatment portion removes at least part of the stenotic lesion (another exemplary treatment step 2112).

In various embodiments and as shown in FIG. 22A, methods 2100 may further comprise the step of ceasing operation of the at least one treatment portion when the luminal size parameter data indicates a preferred luminal size parameter, or (ii) when the type data is no longer indicative of a stenotic lesion (additional exemplary treatment cessation steps 2120).

Figure 22B:
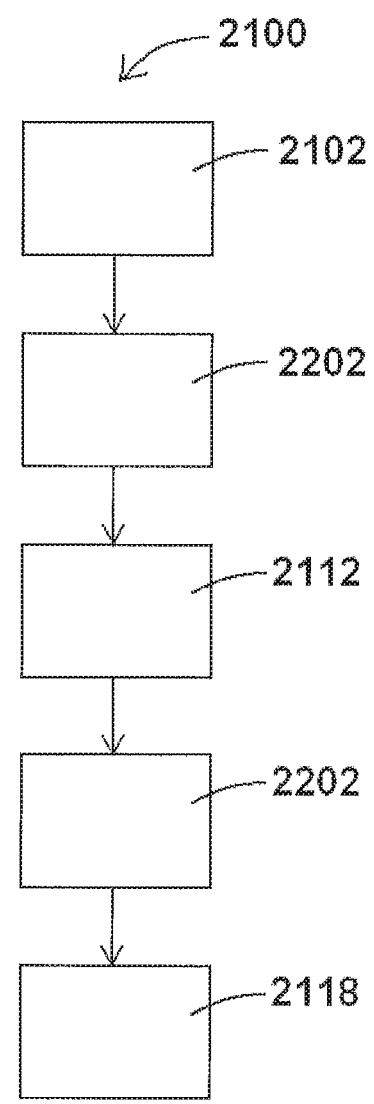

In another exemplary method 2100 of the present disclosure, and as shown in FIG. 22B, method 2100 comprises the steps of positioning a device within a luminal organ, the device comprising at least one typing portion and at least one treatment portion (an exemplary positioning step 2102), operating the at least one typing portion of the device to obtain initial type data indicative of electrical impedance of the luminal organ or a structure, therein (an exemplary typing step 2202), operating the at least one treatment portion if the type data is indicative of a stenotic lesion to remove at least part of the stenotic lesion (an exemplary treatment step 2112), and operating the at least one typing portion of the device again to obtain then-current type data indicative of electrical impedance of the luminal or the structure therein (an exemplary subsequent typing step 2202). In at least one embodiment, method 2100 further comprises repeating steps 2112 and 2202 until the then-current type data does not indicate the presence of the stenotic lesion (another exemplary repeat step 2118).

While various embodiments of devices and systems for removing targeted lesions from vessels and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method of removing at least part of a stenotic lesion within a luminal organ, the method comprising the steps of:
   (a) positioning at least part of a device within a luminal organ at a first location without a stenotic lesion;
   (b) operating the device to obtain a first luminal size parameter and a first measurement indicative of electrical impedance of a luminal organ wall and/or a structure present on the luminal organ wall therein that at least a part of the device is physically touching at the first location wherein the part of the device physically touching at the first location is circumferentially rotatable relative to the device;
   (c) moving at least part of the device to a second location within the luminal organ with a stenotic lesion;
   (d) operating the device to obtain a second luminal size parameter and a second measurement indicative of electrical impedance of the luminal organ or the structure therein that at least part of the device is physically touching at the second location;
   (e) determining whether or not a stenotic lesion is present at either the first location or the second location based on one or more of the first luminal size parameter, the first measurement, the second luminal size parameter, and the second measurement;
   (f) if the stenotic lesion is present, moving at least part of the device having a treatment portion to a stenotic lesion location, wherein the treatment portion is positioned proximal to the circumferentially rotatable part of the device; and
   (g) if the stenotic lesion is present, operating the treatment portion of the device to remove at least part of the stenotic lesion.

2. The method of claim 1, wherein the preferred luminal size parameter is determined based upon the first luminal size parameter and the second luminal size parameter.

3. The method of claim 1, wherein steps (b) and (d) are performed in the presence of a saline injection.

4. The method of claim 1, wherein the step of moving at least part of the device to a second location comprises advancing or retracting at least part of the device within the luminal organ.

5. The method of claim 1, wherein the step of moving at least part of the device to a second location comprises rotating at least part of the device within the luminal organ.

6. The method of claim 1, wherein the first luminal size parameter, the second luminal size parameter, and then-current luminal size parameter(s) are obtained using a detector coupled to the device.

7. The method of claim 1, wherein the first measurement and the second measurement are obtained using a directional sensor coupled to the device.

8. The method of claim 1, further comprising the steps of: selecting an appropriately-sized stent: and implanting the stent into the luminal organ.

9. The method of claim 8, wherein before selecting and implanting the stent, the method further comprises the steps of:
 (h) measuring a then-current luminal size parameter at the stenotic lesion location; (i) comparing the then-current luminal size parameter to either the first luminal size parameter or the second luminal size parameter that is indicative of the stenotic lesion location; (j) if the then-current luminal size parameter does not equal a preferred luminal size parameter, repeating steps (g), (h), and (i) until the then-current luminal size parameter equals or exceeds the preferred luminal size parameter.

10. The method of claim 9, wherein the step of measuring then then-current luminal size parameter at the stenotic lesion location further comprises measuring a then-current measurement indicative of electrical impedance of the luminal organ or structure therein, and wherein the step of comparing the then-current luminal size parameter to either the first luminal size parameter or the second luminal size parameter further comprises comparing either the first measurement or the second measurement to the then-current measurement.

11. The method of claim 10, wherein steps (g), (h), and (i) are repeated if the then-current luminal size parameter does not equal a preferred luminal size parameter or if the then-current measurement is indicative of electrical impedance of the stenotic lesion.

12. The method of claim 9, further comprising the step of: ceasing the operation of the treatment portion of the device when the then-current luminal size parameter equals or exceeds the preferred luminal size parameter.

13. A method for removing at least part of a stenotic lesion from a luminal organ, the method comprising the steps of: positioning a device within a luminal organ at a first location without a stenotic lesion, the device comprising at least one sizing portion, at least one typing portion, and at least one treatment portion; operating the at least one sizing portion of the device to obtain luminal size parameter data; operating the at least one typing portion of the device to physically touch luminal organ wall and/or a structure present on the luminal organ wall obtain type data indicative of electrical impedance of the luminal organ or a structure therein, wherein the typing portion comprises a rotatable portion that is circumferentially rotatable relative to the device; determining the type of tissue or structure from the type data; positioning the device within the luminal organ at a second location with a stenotic lesion, operating the at least one sizing portion of the device to obtain luminal size parameter data; operating the at least one typing portion of the device to physically touch luminal organ wall and/or a structure present on the luminal organ wall obtain type data indicative of electrical impedance of the luminal organ or a structure therein, wherein the typing portion comprises a rotatable portion that is circumferentially rotatable relative to the device:
 determining the tyre of tissue or structure from the type data: operating the at least one treatment portion at the second location within the luminal organ at or near a stenotic lesion, the at least one treatment portion positioned proximal to the circumferentially rotatable portion of the device; whereby operation of the at least one treatment portion is based upon the luminal size parameter data and the type data, whereby operation of the at least one treatment portion removes at least part of the stenotic lesion.

14. The method of claim 13, further comprising the step of:
 ceasing operation of the at least one treatment portion when the luminal size parameter data indicates a preferred luminal size parameter.

15. The method of claim 13, further comprising the step of:
 ceasing operation of the at least one treatment portion when the type data is no longer indicative of electrical impedance of a stenotic lesion.

16. The method of claim 13, wherein the steps of operating the at least one sizing portion and operating the at least one sizing portion are performed in the presence of a saline injection.

17. The method of claim 13, further comprising the steps of: selecting an appropriately-sized stent: and implanting the stent into the luminal organ.

18. A method of removing at least part of a stenotic lesion from a vessel, the method comprising the steps of:
 (a) positioning a device within a luminal organ at a first location without a stenotic lesion, the device comprising at least one typing portion and at least one treatment portion;
 (b) operating the at least one typing portion of the device to obtain initial type data indicative of electrical impedance of the luminal organ or a structure therein, wherein the operating step comprises the typing portion physically touching a luminal organ wall and/or structure present on the luminal organ wall at the first location, and wherein the operating step comprises circumferentially rotating at least a portion of the typing portion relative to the device;
 (c) positioning a device within the luminal organ at a second location with a stenotic lesion, the device comprising at least one typing portion and at least one treatment portion;
 (d) operating the at least one typing portion of the device to obtain initial type data indicative of electrical impedance of the luminal organ or a structure therein, wherein the operating step comprises the typing portion physically touching a luminal organ wall and/or structure present on the luminal organ wall at the second location, and wherein the operating step comprises circumferentially rotating at least a portion of the typing portion relative to the device;
 (e) operating the at least one treatment portion if the type data is indicative of electrical impedance of a stenotic lesion to remove at least part of the stenotic lesion; wherein the at least one treatment portion is positioned proximal to the circumferentially rotatable portion of the device; and (f) operating the at least one typing portion of the device again to obtain then-current type data indicative of electrical impedance of the luminal or the structure therein; and (g) repeating steps (e) and (f) until the then-current type data does not indicate the presence of the stenotic lesion.

19. The method of claim 18, further comprising the steps of: selecting an appropriately-sized stent: and implanting the stent into the luminal organ.

* * * * *